(12) United States Patent
Carling et al.

(10) Patent No.: US 8,492,424 B2
(45) Date of Patent: Jul. 23, 2013

(54) COMPOUNDS ACT AT MULTIPLE PROSTAGLANDIN RECEPTORS GIVING A GENERAL ANTI-INFLAMMATORY RESPONSE

(75) Inventors: William R. Carling, Bishop's Stortford (GB); Jose L. Martos, Basildon Essex (GB); David F. Woodward, Lake Forest, CA (US); Jenny W. Wang, Irvine, CA (US); Jussi J. Kangasmetsa, Essex (GB)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/170,467

(22) Filed: Jun. 28, 2011

(65) Prior Publication Data
US 2012/0165382 A1 Jun. 28, 2012

Related U.S. Application Data

(60) Provisional application No. 61/360,755, filed on Jul. 1, 2010.

(51) Int. Cl.
*A61K 31/415* (2006.01)
*C07D 231/10* (2006.01)

(52) U.S. Cl.
USPC .................................. 514/406; 548/376.1

(58) Field of Classification Search
USPC .................................. 514/406; 548/376.1
See application file for complete search history.

(56) References Cited

U.S. PATENT DOCUMENTS

| 6,511,999 B2 | 1/2003 | Burk et al. |
| 2004/0162323 A1 | 8/2004 | Krauss et al. |
| 2005/0065200 A1 | 3/2005 | Woodward et al. |
| 2007/0060596 A1 | 3/2007 | Giblin et al. |

FOREIGN PATENT DOCUMENTS

| WO | WO 2005/040128 | 5/2005 |
| WO | 2006114313 | 11/2006 |

OTHER PUBLICATIONS

Adrian Hall, et al., Novel Methylene-Linked Heterocyclic EP1 Receptor Antagonists, Biorganic & Medicinal Chemistry Letters, 2008, 18, 1592-1597, Elsevier.

Allergan, Inc., International Search Report PCTUS2011042729, (13 pages) Oct. 10, 2011.
Matias et al., 2004) p. 40 line 19 of appl.
Ho et al., 2003) p. 47 line 9 of appl.
Garcia et al., 2005) p. 47 line 11 of appl.
Pivarcsi et al., 2005) p. 47 line 12 of appl.
Qi et al., 2009 p. 47 line 15 of appl.
Gleissner et al., 2008) p. 47 line 21 of appl.
Zernecke et al., 2008) p. 47 line 30 of appl.
Iwamoto et al., 2008) p. 48 line 3 of appl.
Conti et al., 2001) p. 48 line 7 of appl.
Castellani et al., 2007) p. 48 line 9 of appl.
Remington's Pharmaceutical Sciences, Mack Publishing Company, Easton, Pa., 16th Edition, 1980.

*Primary Examiner* — Samantha Shterengarts
(74) *Attorney, Agent, or Firm* — John E. Wurst; Allergan, Inc.

(57) ABSTRACT

The present invention provides a compound, that is a 1-[(2-{[(alkyl or aryl)methyl]oxy}halo or haloalkyl substituted-phenyl)alkyl]-5-hydrocarbyl or substituted hydrocarbyl-1H-pyrazole carboxylic acid or alkylenylcarboxylic acid or a hydrocarbyl or substituted hydrocarbyl sulfonamide of said carboxylic acid or said alkylenylcarboxylic acid, provided however said compound is not a 3-carboxylic acid, a sulfonamide thereof, or a 3-methylenylcarboxylic acid. The compound may be represented by the following formula

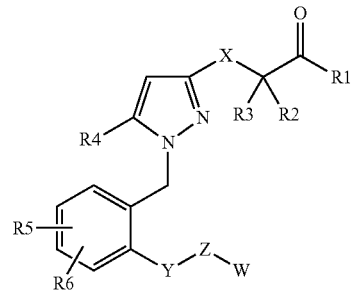

Wherein $R_1$, $R_2$, $R_3$, $R_4$, $R_5$, $R_6$, X, W, X and Y are as defined in the specification. The compounds may be administered to treat DP1, FP, EP1, TP and/or EP4 receptor mediated diseases or conditions.

22 Claims, 13 Drawing Sheets

Preparation of Example 1

Preparation of Examples 2-4

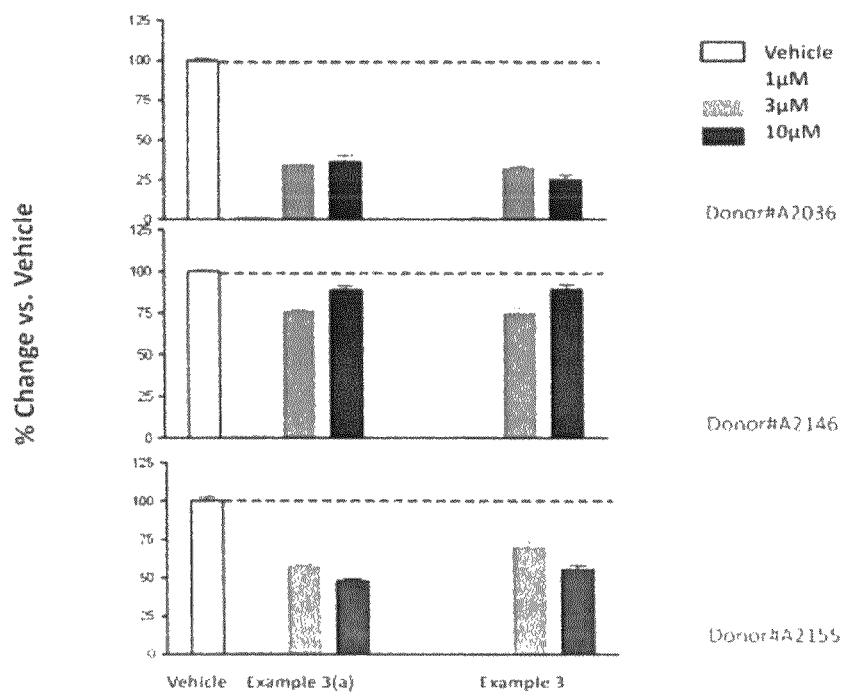
Figure 2. IL-8 Secretion from TNFα-Induced Human Macrophages

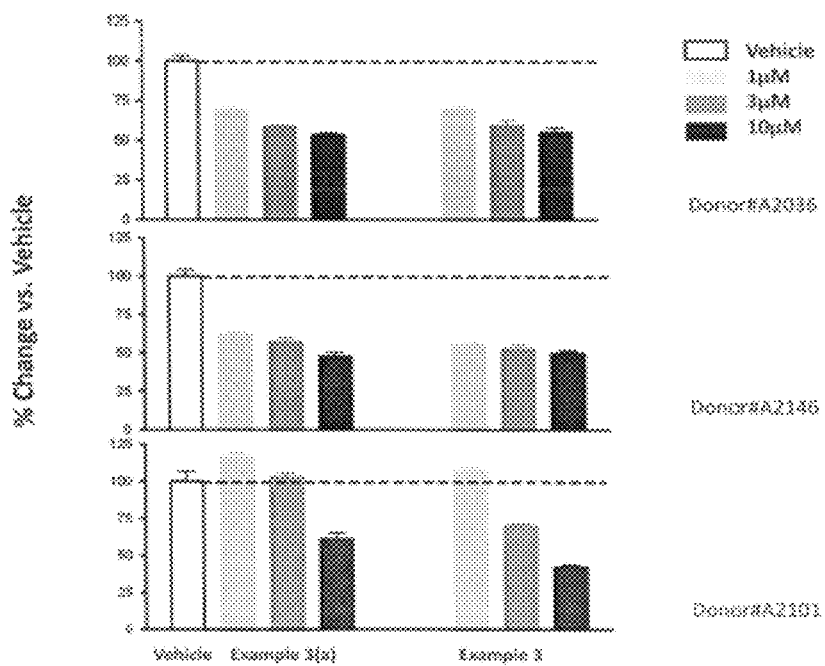
Figure 3. MCP-1 Secretion from TNFα-Induced Human Macrophages

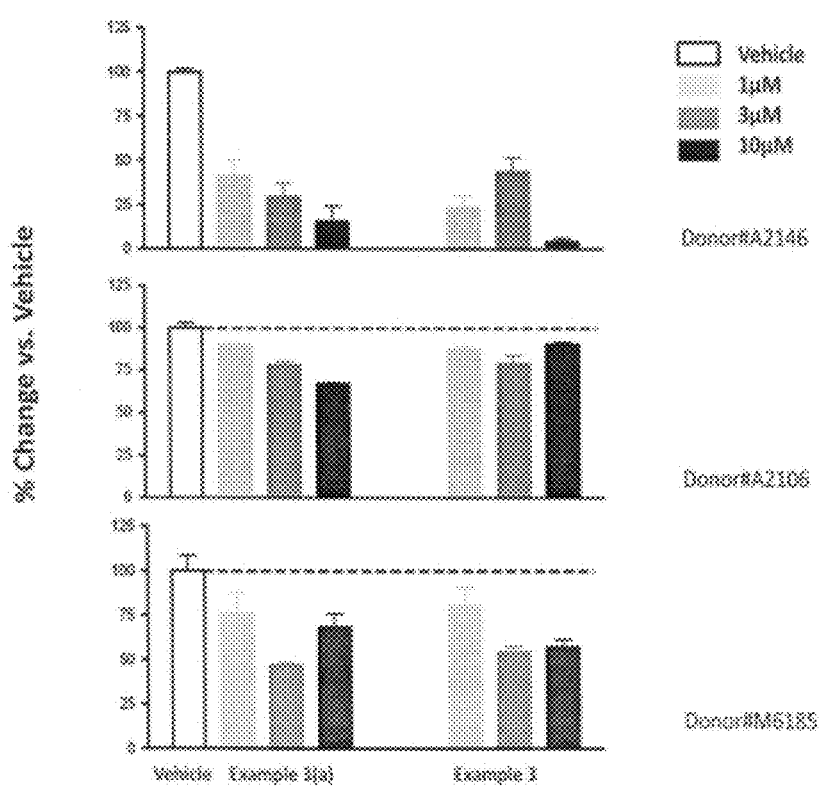

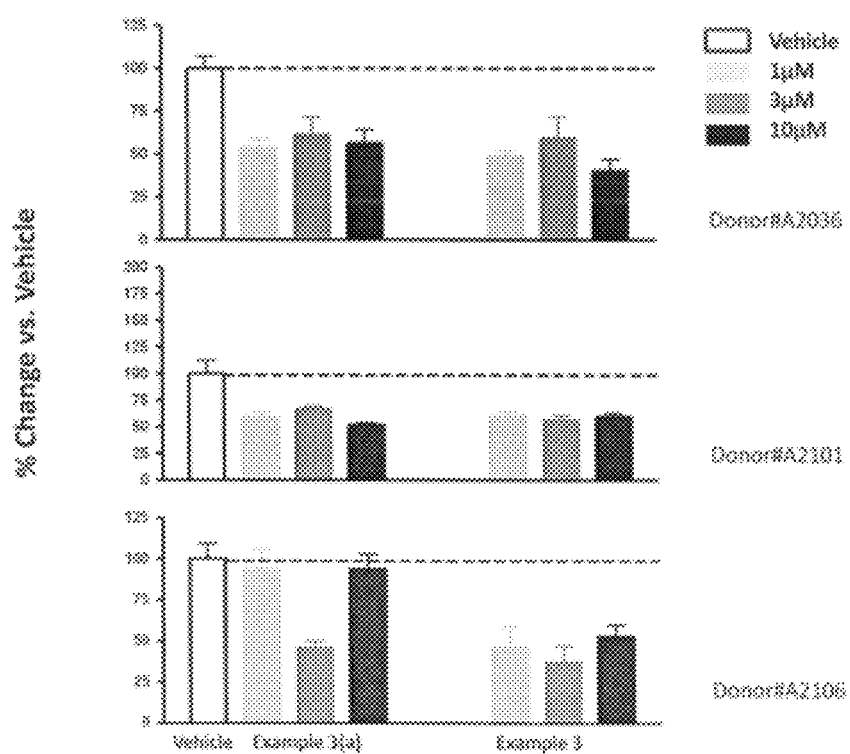

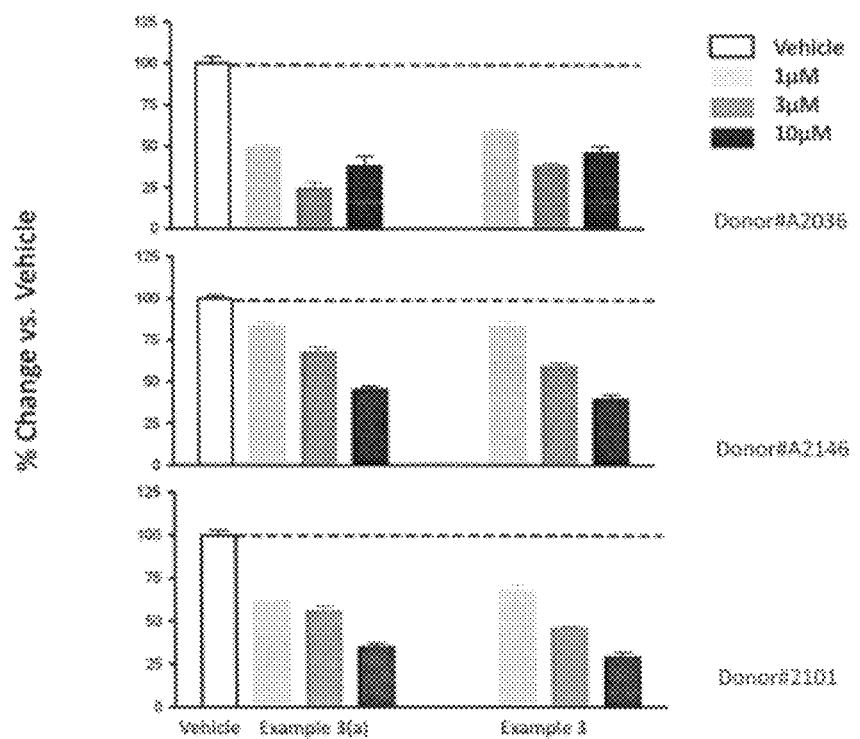
Figure 6. RANTES Secretion from LPS-Induced Human Macrophages

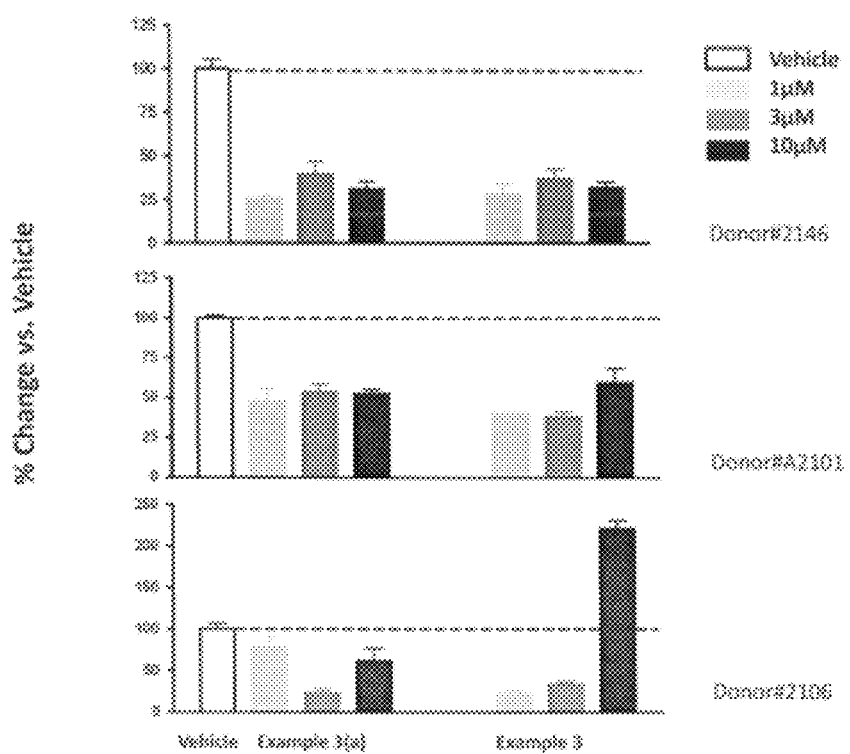

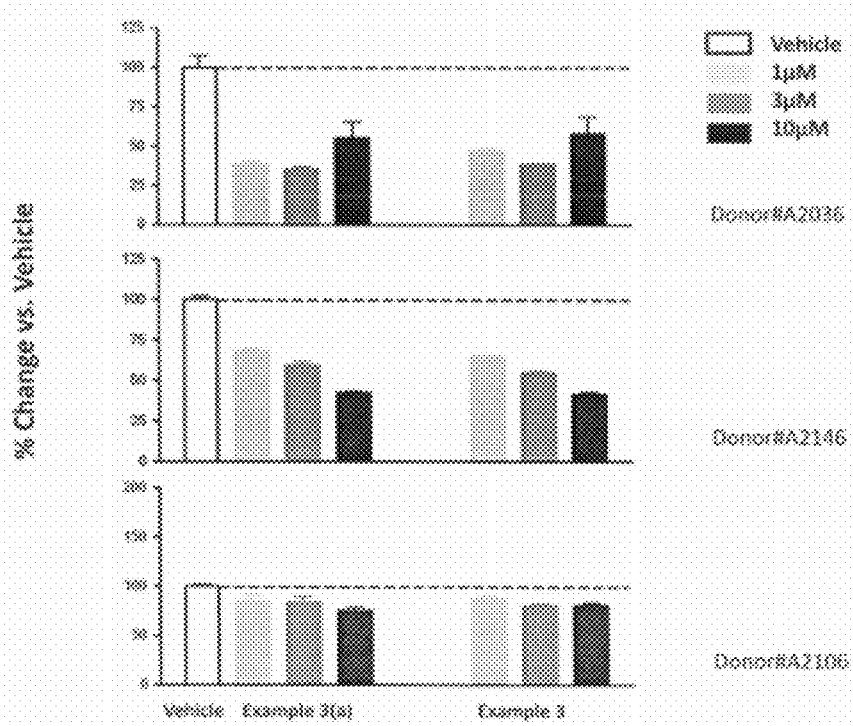

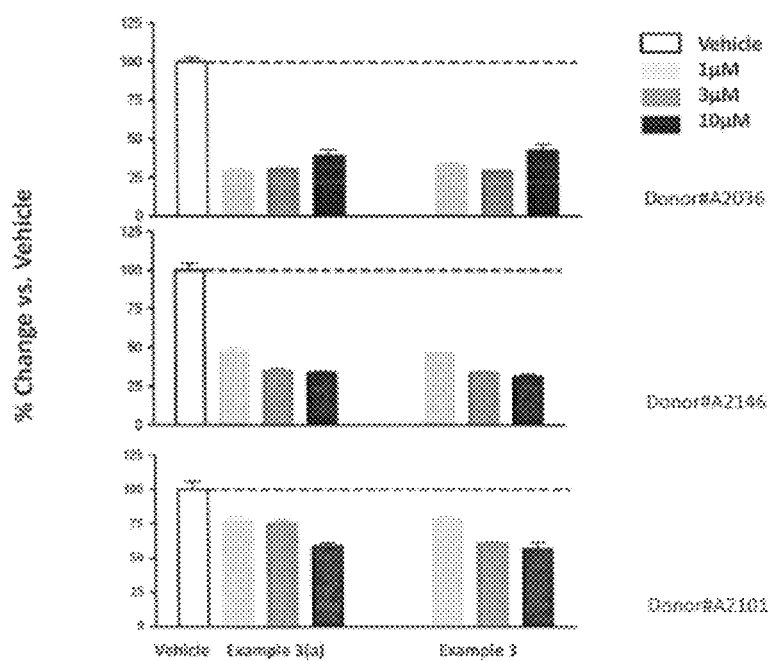

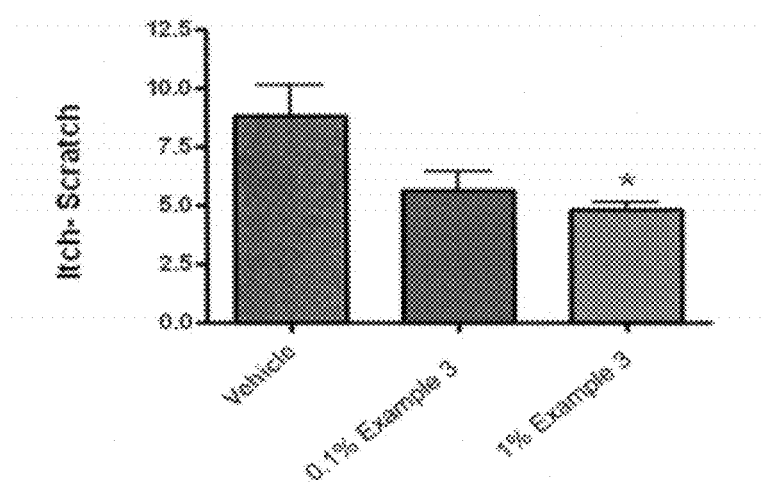
Figure 10. Conjuctival Itch Experiment

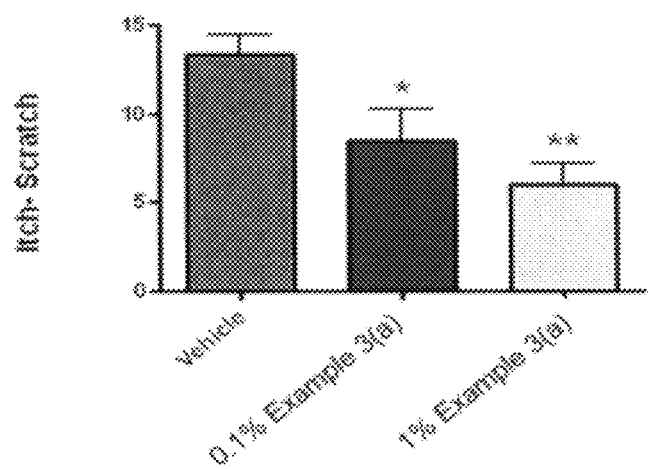
Figure 11. Conjuctival Itch Experiment

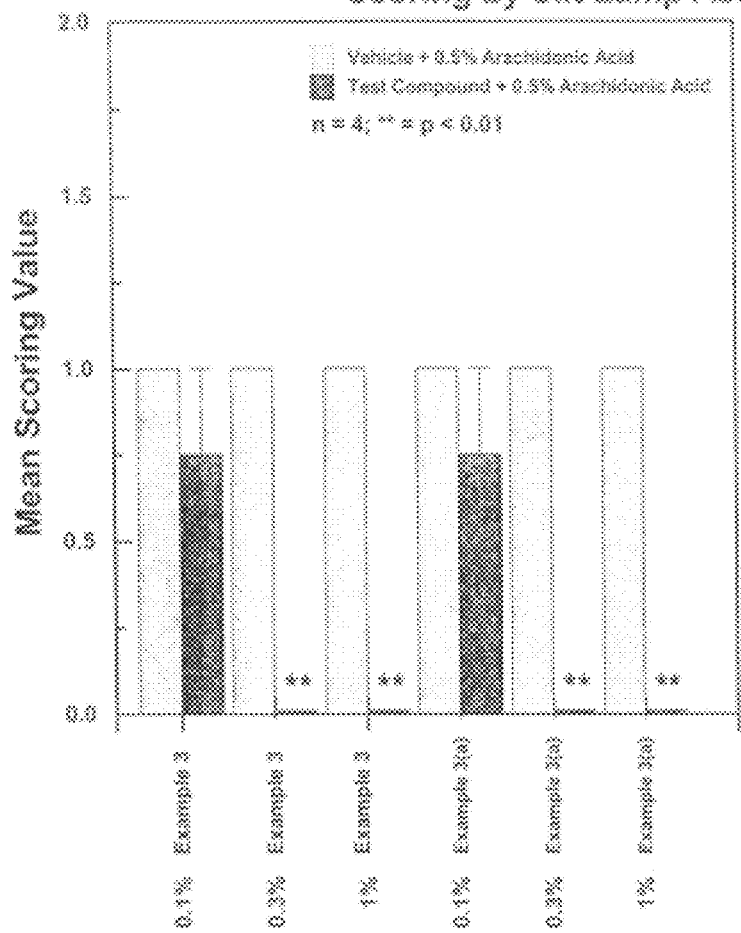
Figure 12. 0.5% Arachidonic Acid-Induced Anterior Chamber Leukocyte Infiltration in Pigmented Rabbits - Scoring by Slit Lamp Assessment

COMPOUNDS ACT AT MULTIPLE PROSTAGLANDIN RECEPTORS GIVING A GENERAL ANTI-INFLAMMATORY RESPONSE

CROSS REFERENCE TO RELATED APPLICATIONS

This application claims the benefit of U.S. Provisional Patent Application Ser. No. 61/360,755 which was filed on Jul. 1, 2010 and is hereby incorporated by reference in its entirety.

BACKGROUND OF THE INVENTION

1. Field of the Invention

This invention relates to compounds, to processes for their preparation, to pharmaceutical compositions containing them and to their use in medicine, in particular their use in the treatment of conditions mediated by the action of ligands for the $DP_1$, FP, TP, $EP_1$ and $EP_4$ prostaglandin (PG) receptors. The present compounds have the general structure shown below and act at different prostaglandin receptors to thereby provide a general anti-inflammatory response.

2. Summary of the Related Art

The $EP_1$ receptor is a 7-transmembrane receptor and its natural ligand is the prostaglandin $PGE_2$. $PGE_2$ also has affinity for the other EP receptors (types $EP_2$, $EP_3$ and $EP_4$). The $EP_1$ receptor is associated with smooth muscle contraction, pain (in particular inflammatory, neuropathic and visceral), inflammation, allergic activities, renal regulation and gastric or enteric mucus secretion.

Prostaglandin $E_2$ ($PGE_2$) exerts allodynia through the $EP_1$ receptor subtype and hyperalgesia through $EP_2$ and $EP_3$ receptors in the mouse spinal cord. Furthermore, it has been shown that in the $EP_1$ knock-out mouse pain-sensitivity responses are reduced by approximately 50%. $EP_1$ receptor antagonist (ONO-8711) reduces hyperalgesia and allodynia in a rat model of chronic constriction injury and inhibits mechanical hyperalgesia in a rodent model of post-operative pain. The efficacy of $EP_1$ receptor antagonists in the treatment of visceral pain in a human model of hypersensitivity has been demonstrated. Thus, selective prostaglandin ligands, agonists or antagonists, depending on which prostaglandin E receptor subtype is being considered, have anti-inflammatory, antipyretic and analgesic properties similar to a conventional non-steroidal anti-inflammatory drug, and in addition, inhibit hormone-induced uterine contractions and have anti-cancer effects. These compounds have a diminished ability to induce some of the mechanism-based side effects of NSAIDs which are indiscriminate cyclooxygenase inhibitors. In particular, the compounds have a reduced potential for gastrointestinal toxicity, a reduced potential for renal side effects, a reduced effect on bleeding times and a lessened ability to induce asthma attacks in aspirin-sensitive asthmatic subjects. Moreover, as a result of sparing potentially beneficial prostaglandin pathways, these agents may have enhanced efficacy over NSAIDS and/or COX-2 inhibitors.

(See Pub. No. US 2005/0065200 for other diseases that may be treated by EP4 receptor antagonists.)

The TP (also known as $TxA_2$) receptor is a prostanoid receptor subtype stimulated by the endogenous mediator thromboxane. Activation of this receptor results in various physiological actions primarily incurred by its platelet aggregatory and smooth muscle constricting effects, thus opposing those of prostacyclin receptor activation.

TP receptors have been identified in human kidneys in the glomerulus and extraglomerular vascular tissue. Activation of TP receptors constricts glomerular capillaries and suppresses glomerular filtration rates indicating that TP receptor antagonists could be useful for renal dysfunction in glomerulonephritis, diabetes mellitus and sepsis.

Activation of TP receptors induces bronchoconstriction, an increase in microvascular permeability, formation of mucosal edema and mucus secretion, which are typical characteristic features of bronchial asthma. TP antagonists have been investigated as potential asthma treatments resulting in, for example, orally active Seratrodast (AA-2414). Ramatroban is another TP receptor antagonist currently undergoing phase III clinical trials as an anti-asthmatic compound.

Since the $DP_1$ receptor may trigger an asthmatic response in certain individuals, compounds that have $DP_1$ antagonist properties may be useful as anti-asthmatic drugs. (See Pub. No. 2004/0162323 for the disclosure of other diseases and conditions that may be treated with DP antagonists.)

Finally, the FP receptor modulates intraocular pressure and mediates smooth muscle contraction of the sphincter muscles in the gastrointestinal tract and the uterus. Thus, antagonists of the FP receptor are useful for treating reproductive disorders. (See U.S. Pat. No. 6,511,999 for other diseases and conditions that may be treated with FP receptor antagonists.)

As further background for the present invention, see US Published Patent Application 2007/0060596.

BRIEF SUMMARY OF THE INVENTION

This invention provides compounds, that are 1-[(2-{[(alkyl or aryl)methyl]oxy}halo or haloalkyl substituted-phenyl)alkyl]-5-hydrocarbyl or 5-substituted hydrocarbyl-1H-pyrazole carboxylic acid or alkylenylcarboxylic acid or a hydrocarbyl or substituted hydrocarbyl sulfonamide of said carboxylic acid or said alkylenylcarboxylic acid, provided however, said compound is not a 3-carboxylic acid, a sulfonamide thereof, or a 3-methylenylcarboxylic acid.

Said alkylenyl may be ethylenyl.

The following terms are used to define the disclosed invention.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, phosphate, thiol, etc.

"Methylenyl" refers to a —$CH_2$— linking group.

"Ethylenyl" refers to a —$CH_2CH_2$— linking group.

"Alkylenyl" refers to a divalent alkyl linking group.

"Alkyl" refers to a straight-chain, branched or cyclic saturated aliphatic hydrocarbon. Preferably, the alkyl group has 1 to 12 carbons. More preferably, it is an alkyl of from 4 to 10 carbons, most preferably 4 to 8 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, $NO_2$, halogen, dimethyl amino, and SH.

"Cycloalkyl" refers to a cyclic saturated aliphatic hydrocarbon group. Preferably, the cycloalkyl group has 3 to 12 carbons. More preferably, it has from 4 to 7 carbons, most preferably 5 or 6 carbons.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of alkyl, hydroxyl, halogen, $COOR^6$, $NO_2$, $CF_3$, $N(R^6)_2$, $CON(R^6)_2$, $SR^6$, sulfoxy, sulfone, CN and $OR^6$, wherein $R^6$ is alkyl.

"Carbocyclic aryl" refers to an aryl group wherein the ring atoms are carbon.

"Heteroaryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like. Preferably; the heteroaryl group has from 2 to 10 carbons. More preferably, it has from 3 to 10 carbons, most preferably 3 carbons.

Said 5-hydrocarbyl may be 5-methyl and said (halo or haloalkyl substituted-phenyl)alkyl may be (halo or haloalkyl substituted-phenyl)methyl.

The compound according to the present invention may be a 1-[(2-{[(alkyl)methyl]oxy} halo or haloalkyl-substituted phenyl)methyl]-5-methyl-1H-pyrazole-3-ethylenylcarboxylic acid, or a 1-[(2-{[(aryl)methyl]oxy} halo or haloalkyl-substituted phenyl)methyl]-5-methyl-1H-pyrazole-3-carboxylic acid fluoro-substituted alkylsulfonamide or alkylenylcarboxylic acid fluoro-substituted alkylsulfonamide wherein said halo is selected from the group consisting of fluoro, chloro and bromo.

Said halo or haloalkyl-substituted phenyl may be selected from the group consisting of trifluoromethylphenyl, chlorophenyl and bromophenyl.

Preferably, the compound of the present invention may be a trifluoromethylsulfonamide wherein said aryl is chlorophenyl.

Most preferably said alkyl comprising said -{[(alkyl)methyl]oxy} is 3-pentyl. or cyclopentyl.

The invention further relates to pharmaceutical compositions containing the above compounds in combination with a pharmaceutically-acceptable excipient and to their use in medicine, in particular their use in the treatment of conditions mediated by the action of ligands for the $DP_1$, FP, $EP_1$ and $EP_4$ prostaglandin (PG) receptors. The compounds of this invention are also useful for treating conditions mediated by the action of ligands for the thromboxane (TP) receptor.

Some embodiments of the present invention include:
1. A compound, that is a 1-[(2-{[(alkyl or aryl)methyl]oxy} halo or haloalkyl substituted-phenyl)alkyl]-5-hydrocarbyl or substituted hydrocarbyl-1H-pyrazole carboxylic acid or alkylenylcarboxylic acid or a hydrocarbyl or substituted hydrocarbyl sulfonamide of said carboxylic acid or said alkylenylcarboxylic acid, provided however said compound is not a 3-carboxylic acid, a sulfonamide thereof, or a 3-methylenylcarboxylic acid.
2. A compound according to paragraph 1 wherein said 5-hydrocarbyl is 5-methyl.
3. A compound according to paragraph 2 wherein said halo or haloalkyl substituted-phenylalkyl is halo or haloalkyl substituted-phenyl)methyl.
4. A compound according to paragraph 3, that is a 1-[(2-{[(alkyl)methyl]oxy} halo or haloalkyl-substituted phenyl)methyl]-5-methyl-1H-pyrazole-3-ethylenylcarboxylic acid, wherein said halo is selected from the group consisting of fluoro, chloro and bromo.
5. A compound according to paragraph 3, that is a 1-[(2-{[(aryl)methyl]oxy} halo or haloalkyl-substituted phenyl)methyl]-5-methyl-1H-pyrazole-3-carboxylic acid fluoro-substituted alkylsulfonamide or alkylenylcarboxylic acid fluoro-substituted alkylsulfonamide, wherein said halo is selected from the group consisting of fluoro, chloro and bromo.
6. The compound of paragraph 4 wherein said halo or haloalkyl-substituted phenyl is selected from the group consisting of trifluoromethylphenyl, chlorophenyl and bromophenyl.
7. The compound of paragraph 3 wherein said halo or haloalkyl-substituted phenyl is selected from the group consisting of trifluoromethylphenyl, chlorophenyl and bromophenyl.
8. The compound of paragraph 1 wherein said compound is a trifluoromethylsulfonamide and said aryl is chlorophenyl.
9. The compound of paragraph 6 wherein said alkyl is 3-pentyl.
10. The compound of paragraph 6 wherein said alkyl is cyclopentyl.
11. A compound having the following formula

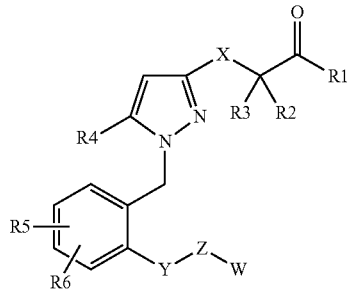

Wherein $R_1$ is selected from the group consisting of $OR_7$, $N(R_7)_2$, and $N(R_7)SO_2R_7$ wherein $R_7$ is selected from the group consisting of H, alkyl and aryl, wherein said alkyl and aryl may be substituted with fluoro;
$R_2$ is selected from the group consisting of H and alkyl;
$R_3$ is selected from the group consisting of H and alkyl; wherein $R_2$ and $R_3$, individually or together, can form a cycloalkyl ring;
X is $(CH_2)_n$ wherein n is 0 or an integer of from 1 to 3; provided however that when n is 0 or 1, $R_1$ is not $OR_7$ or $NR_2$;
$R_4$ is selected from the group consisting of H, alkyl and fluoroalkyl;
$R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;
$R_6$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy and aryloxy;
Z is $(CH_2)_m$ wherein m is 0 or an integer of from 1 to 3;
Y is selected from the group consisting of O, S, SO, $SO_2$ and $(CH_2)_p$, wherein p is 0 or an integer of from 1 to 3; and
W is selected from the group consisting of alkyl and aryl.
12. The compound of paragraph 11 wherein $R_1$ is selected from the group consisting of OH and $NHSO_2CF_3$.
13. The compound of paragraph 12 wherein $R_2$ and $R_3$ are H.
14. The compound of paragraph 13 wherein $R_4$ is alkyl.

15. The compound of paragraph 14 wherein $R_4$ is methyl.
16. The compound of paragraph 12 wherein $R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy, aryloxy and $R_6$ is H.
17. The compound of paragraph 16 wherein $R_5$ is selected from the group consisting of H, alkyl, alkoxy, halogen and fluorinated alkyl and alkoxy.
18. The compound of paragraph 17 wherein $R_5$ is selected from the group consisting of chloro, bromo and trifluoromethyl.
19. The compound of paragraph 12 wherein Z is $(CH_2)$.
20. The compound of paragraph 12 wherein Y is O.
21. The compound of paragraph 12 wherein W is selected from the group consisting of alkyl, benzylyl and halogen-substituted benzyl.
22. The compound of paragraph 21 wherein W is selected from the group consisting of alkyls having from 4 to 7 carbon atoms.
23. The compound of paragraph 22 wherein W is cyclopentyl.
24. The compound of paragraph 11, wherein said compound is selected from the group consisting of N-(3-{1-[5-Chloro-2-(4-chloro-benzyloxy)-benzyl]-5-methyl-1H-pyrazol-3-yl}-propionyl)-C,C,C-trifluoromethanesulfonamide,
3-{1-[5-Chloro-2-(2-ethyl-butoxy)-benzyl]-5-methyl-1H-pyrazol-3-yl}-propionic acid,
3-{[5-Bromo-2-(2-ethyl-butoxy)-benzyl]-5-methyl-1H-pyrazol-3-yl}-propionic acid,
3-[1-(5-Bromo-2-cyclopentylmethoxybenzyl)-5-methyl-1H-pyrazol-3-yl]-propionic acid,
and
3-[1-(2-Cyclopentylmethoxy-5-trifluoromethylbenzyl)-5-methyl-1H-pyrazol-3-yl]-propionic acid.
25. A method of making 3-{1-[5-Halo or haloalkyl-2-(4-chloro-benzyloxy or 4-chloro-alkyloxy)-benzyl]-5-methyl-1H-pyrazol-3-yl}-propionic acid which comprises hydrolyzing a 3-{1-[5-Halo or haloalkyl-2-(4-chloro-benzyloxy or 4-chloro-alkyloxy)-benzyl]-5-methyl-1H-pyrazol-3-yl}-propionic acid methyl ester, to yield 3-{1-[5-Halo or haloalkyl-2-(4-chloro-benzyloxy or 4-chloro-alkyloxy)-benzyl]-5-methyl-1H-pyrazol-3-yl}-propionic acid.
26. The method of paragraph 25 wherein said halo is selected from the group consisting of fluoro, chloro and bromo.
27. The method of paragraph 26 wherein said haloalkyl is trifluoromethyl.
28. The method of paragraph 25 wherein said alkyloxy is selected from the group consisting of alkyloxy wherein said alkyl comprises from 4 to 7 carbon atoms.
29. The method of paragraph 28 wherein said alkyl is selected from the group consisting of 3-pentyl and cyclopentylmethyl.
30. The method of paragraph 25 wherein said 3-{1-[5-Halo or haloalkyl-2-(4-chloro-benzyloxy or 4-chloro-alkyloxy)-benzyl]-5-methyl-1H-pyrazol-3-yl}-propionic acid is prepared by hydrogenating the corresponding (E)-3-{1-[5-Halo or haloalkyl-2-(4-chloro-benzyloxy or 4-chloro-alkyloxy)-benzyl]-5-methyl-1H-pyrazol-3-yl}-acrylic acid methyl ester to yield 3-{1-[5-Halo or haloalkyl-2-(4-chloro-benzyloxy or 4-chloro-alkyloxy)-benzyl]-5-methyl-1H-pyrazol-3-yl}-propionic acid.
31. The method of paragraph 30 wherein said hydrogenation is carried out in the presence of a platinum catalyst.
32. The method of paragraph 30 wherein said (E)-3-{1-[5-Halo or haloalkyl-2-(4-chloro-benzyloxy or 4-chloro-alkyloxy)-benzyl]-5-methyl-1H-pyrazol-3-yl}-acrylic acid methyl ester is prepared by reacting trimethylphosphonoacetate with the corresponding {1-[5-Halo or haloalkyl-2-(4-chloro-benzyloxy or 4-chloro-alkyloxy)-benzyl]-5-methyl-1H-pyrazole-3-carbaldehyde to yield said (E)-3-{1-[5-Halo or haloalkyl-2-(4-chloro-benzyloxy or 4-chloro-alkyloxy)-benzyl]-5-methyl-1H-pyrazol-3-yl}-acrylic acid methyl ester.
33. A method of making N-(3-{1-[5-halo or haloalkyl-2-(4-chloro-benzyloxy or 4-chloro-alkyloxy)-benzyl]-5-methyl-1H-pyrazol-3-yl}-propionyl)-C,C,C-trifluoro-methane-sulfonamide comprising the step of (a) reacting the corresponding. 3-{1-[5-Halo or haloalkyl-2-(4-chloro-benzyloxy or 4-chloro-alkyloxy)-benzyl]-5-methyl-1H-pyrazol-3-yl}-propionic acid with cyanuric fluoride to yield 3-{1-[5-halo or haloalkyl-2-(4-chloro-benzyloxy or 4-chloro-alkyloxy)-benzyl]-5-methyl-1H-pyrazol-3-yl}-propionyl fluoride and (b) reacting said 0.3-{1-[5-halo or haloalkyl-2-(4-chloro-benzyloxy or 4-chloro-alkyloxy)-benzyl]-5-methyl-1H-pyrazol-3-yl}-propionyl fluoride with trifluoromethanesulfonamide to yield N-(3-{1-[5-halo or haloalkyl-2-(4-chloro-benzyloxy or 4-chloro-alkyloxy)-benzyl]-5-methyl-1H-pyrazol-3-yl}-propionyl)-C,C,C-trifluoro-methanesulfonamide.
34. The method of paragraph 33 wherein said step (a) is carried out in the presence of pyridine.
35. The method of paragraph 33 wherein said step (b) is carried out in the presence of DMAP.
36. A method comprising administering a compound having the following formula Wherein $R_1$ is selected from the group consisting of $OR_2$, $N(R_2)_2$, and $N(R_2)SO_2R_2$ wherein $R_7$ is selected from the group consisting of H, alkyl and aryl, wherein said alkyl and aryl may be substituted with fluoro;
$R_2$ is selected from the group consisting of H and alkyl;
$R_3$ is selected from the group consisting of H and alkyl; wherein $R_2$ and $R_3$, individually or together, can form a cycloalkyl ring;
X is $(CH_2)_n$ wherein n is 0 or an integer of from 1 to 3, provided however that when n is 0 or 1, $R_1$ is not $OR_7$. or $NR_2$;
$R_4$ is selected from the group consisting of H, alkyl and fluoroalkyl;
$R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;
$R_6$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy and aryloxy;
Z is $(CH_2)_m$ wherein m is 0 or an integer of from 1 to 3;
Y is selected from the group consisting of O, S, SO, $SO_2$ and $(CH_2)_p$, wherein p is 0 or an integer of from 1 to 3; and
W is selected from the group consisting of alkyl and aryl.

37. The method of paragraph 36 wherein said compound is administered to treat DP1, FP, EP1, TP and/or EP4 receptor mediated diseases or conditions.
38. The method of paragraph 37 wherein said condition or disease is related to inflammation.
39. The method of paragraph 37 wherein said DP1, FP, EP1, TP and/or EP4 receptor mediated condition or disease is selected from the group consisting of allergic conditions, asthma, allergic asthma, allergic rhinitis, uveitis and related disorders, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anticoagulation, diseases requiring control of bone formation and resorption, fertility disorders, gangrene, glaucoma, hyperpyrexia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, rheumatoid arthritis, pain, perennial rhinitis, pulmonary congestion, pulmonary hypotension, Raynaud's disease, rejection in organ transplant and by-pass surgery, respiratory conditions, hirsutism, rhinorrhea, shock, sleep disorders, and sleep-wake cycle disorders.
40. The method of paragraph 37 wherein said compound is administered as a surgical adjunct in ophthalmology for cataract removal and artificial lens insertion, ocular implant procedures, photorefractive radial keratotomy and other ophthalmogical laser procedures.
41. The method of paragraph 37 wherein said compound is administered as a surgical adjunct in a procedure involving skin incisions, relief of pain and inflammation and scar formation/keloids post-surgery, for treating sports injuries and general aches and pains in muscles and joints.
42. The method of paragraph 37 wherein said $DP_1$, FP, $EP_1$, TP, and/or $EP_4$ receptor mediated condition or disease is an $EP_1$ and/or $EP_4$ receptor mediated condition or disease.
43. The method of paragraph 42 wherein said $DP_1$, FP, $EP_1$, TP and/or $EP_4$ receptor mediated condition or disease is an allergic condition.
44. The method of paragraph 37 wherein said condition is dermatological allergy.
45. The method of paragraph 37 wherein said condition is an ocular allergy.
46. The method of paragraph 37 wherein said condition is a respiratory allergy.
47. The method of paragraph 37 wherein said condition or disease is selected from the group consisting of nasal congestion, rhinitis, and asthma.
48. The method of paragraph 37 wherein said condition or disease is related to pain.
49. The method of paragraph 37 wherein said condition or disease is selected from the group consisting of arthritis, migraine, and headache.
50. The method of paragraph 37 wherein said condition or disease is associated with the gastrointestinal tract.
51. The method of paragraph 37 wherein said condition or disease is selected from the group consisting of peptic ulcer, heartburn, reflux esophagitis, erosive esophagitis, non-ulcer dyspepsia, infection by *Helicobacter pylori*, alrynitis, and irritable bowel syndrome.
52. The method of paragraph 37 wherein said condition or disease is selected from the group consisting of hyperalgesia and allodynia.
53. The method of paragraph 37 wherein said condition or disease is related to mucus secretion.
54. The method of paragraph 37 wherein said mucus secretion is gastrointestinal.
55. The method of paragraph 37 wherein said mucus secretion occurs in the nose, sinuses, throat, or lungs.
56. The method of paragraph 37 wherein said condition or disease is related to abdominal cramping.
57. The method of paragraph 37 wherein said condition or disease is irritable bowel syndrome.
58. The method of paragraph 37 wherein said condition or disease is a bleeding disorder.
59. The method of paragraph 37 wherein said condition or disease is a sleep disorder.
60. The method of paragraph 37 wherein said condition or disease is mastocytosis.
61. The method of paragraph 37 wherein said condition or disease is associated with elevated body temperature.
62. The method of paragraph 37 wherein said condition or disease is associated with ocular hypertension and glaucoma.
63. The method of paragraph 37 wherein said condition or disease is associated with ocular hypotension.
64. The method of paragraph 37 wherein said condition relates to surgical produres to treat pain, inflammation and other unwanted sequelae wherein said surgical procedure includes incision, laser surgery or implantation.
65. The method of paragraph 37 where said condition is related to pain and inflammation and post-surgical scar and keloid formation.
66. A pharmaceutical product comprising a compound having the following formula

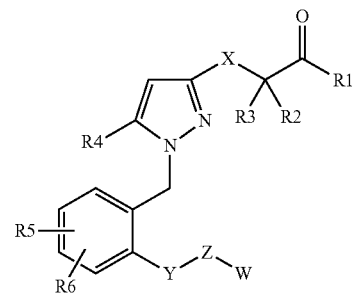

Wherein $R_1$ is selected from the group consisting of $OR_7$, $N(R_7)_2$, and $N(R_7)SO_2R_7$ wherein $R_7$ is selected from the group consisting of H, alkyl and aryl, wherein said alkyl and aryl may be substituted with fluoro;
$R_2$ is selected from the group consisting of H and alkyl;
$R_3$ is selected from the group consisting of H and alkyl; wherein $R_2$ and $R_3$, individually or together, can form a cycloalkyl ring;
X is $(CH_2)_n$ wherein n is 0 or an integer of from 1 to 3; provided however that when n is 0 or 1, $R_1$ is not $OR_7$. or $NR_2$;
$R_4$ is selected from the group consisting of H, alkyl and fluoroalkyl;
$R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;
$R_6$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy and aryloxy;
Z is $(CH_2)_m$ wherein m is 0 or an integer of from 1 to 3;
Y is selected from the group consisting of O, S, SO, $SO_2$ and $(CH_2)_p$, wherein p is 0 or an integer of from 1 to 3; and, W is selected from the group consisting of alkyl and aryl or a pharmaceutically acceptable salt or a prodrug thereof, wherein said product is packaged and labeled for the treatment or prevention of a disease or condition selected from the group consisting of uveitis, allergic conditions, asthma, allergic asthma, allergic rhinitis, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, fertility disorders, hyperpyrexia, gangrene, glaucoma, hypothermia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, pain, perennial rhinitis, pulmonary congestion, pulmonary hypotension, Raynaud's disease, rejection in organ transplant and by-pass surgery, respiratory conditions, rheumatoid arthritis, rhinorrhea, shock, sleep disorders, sleep-wake cycle disorders, sports injuries, muscle aches and pains, and surgical adjunct for minimizing pain, inflammation and scar/keloid formation.

67. A pharmaceutical composition comprising a compound having the following formula

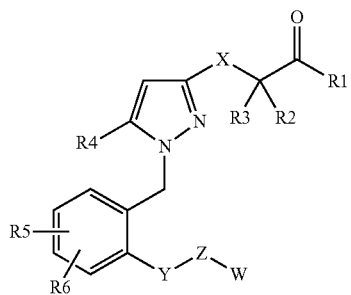

Wherein $R_1$ is selected from the group consisting of $OR_7$, $N(R_7)_2$, and $N(R_7)SO_2R_7$ wherein $R_7$ is selected from the group consisting of H, alkyl and aryl, wherein said alkyl and aryl may be substituted with fluoro;
$R_2$ is selected from the group consisting of H and alkyl;
$R_3$ is selected from the group consisting of H and alkyl; wherein $R_2$ and $R_3$, individually or together, can form a cycloalkyl ring;
X is $(CH_2)_n$ wherein n is 0 or an integer of from 1 to 3; provided however that when n is 0 or 1, $R_1$ is not $OR_7$. or $NR_2$;
$R_4$ is selected from the group consisting of H, alkyl and fluoroalkyl;
$R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;
$R_6$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy and aryloxy;
Z is $(CH_2)_m$ wherein m is 0 or an integer of from 1 to 3;
Y is selected from the group consisting of O, S, SO, $SO_2$ and $(CH_2)_p$, wherein p is 0 or an integer of from 1 to 3; and
W is selected from the group consisting of alkyl and aryl or a pharmaceutically acceptable salt or a prodrug thereof, and a pharmaceutically acceptable excipient.

BRIEF DESCRIPTION OF THE DRAWINGS

FIG. 2 shows modulating the secretion of IL-8 from human macrophages stimulated by TNFα (n=three donors, normalized by cell viability);
FIG. 3 shows modulating the secretion of MCP-1 from human macrophages stimulated by TNFα (n=three donors, normalized by cell viability);
FIG. 4 shows modulating the secretion of TNFα from human macrophages stimulated by LPS (n=three donors, normalized by cell viability);
FIG. 5 shows modulating MDC secretion from human macrophages stimulated by TNFα (n=three donors, normalized by cell viability);
FIG. 6 shows modulating RANTES secretion from human macrophages stimulated by LPS (n=three donors, normalized by cell viability);
FIG. 7 shows modulating MDC secretion from human macrophages stimulated by LPS (n=three donors, normalized by cell viability);
FIG. 8 shows modulating MIP-1$_\beta$ secretion from human macrophages stimulated by TNFα (n=three donors, normalized by cell viability);
FIG. 9 shows modulating RANTES secretion from human macrophages stimulated by TNFα (n=three donors, normalized by cell viability);
FIG. 10 shows the effect of certain compounds of the invention on allergic conjunctival itch;
FIG. 11 shows the effect of certain compounds of the invention on allergic conjunctival itch; and,
FIG. 12 shows that certain compounds of the invention have a dose dependent effect when tested in a model for uveitis.

DETAILED DESCRIPTION OF THE INVENTION

The present invention provides compounds having the general formula:

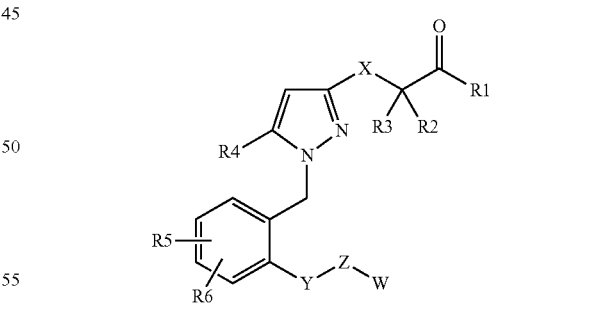

Wherein $R_1$ is selected from the group consisting of $OR_7$, $N(R_7)_2$, and $N(R_7)SO_2R_7$ wherein $R_7$ is selected from the group consisting of H, alkyl and aryl, wherein said alkyl and aryl may be substituted with fluoro or fluoroalkyl;
$R_2$ is selected from the group consisting of H and alkyl;
$R_3$ is selected from the group consisting of H and alkyl; wherein $R_2$ and $R_3$, individually or together, can form a cycloalkyl ring;
X is $(CH_2)_n$ wherein n is 0 or an integer of from 1 to 3; provided however that when n is 0 or 1, $R_1$ is not $OR_7$. or $NR_2$;

$R_4$ is selected from the group consisting of H, alkyl and fluoroalkyl;

$R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;

$R_6$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy and aryloxy;

Z is $(CH_2)_m$ wherein m is 0 or an integer of from 1 to 3;

Y is selected from the group consisting of O, S, SO, $SO_2$ and $(CH_2)_p$, wherein p is 0 or an integer of from 1 to 3;

W is selected from the group consisting of alkyl and aryl;

Preferably, $R_1$ is selected from the group consisting of OH and $NHSO_2CF_3$;

Preferably, $R_2$ is H;

Preferably, $R_3$ is H;

Preferably, $R_1$ is alkyl;

More preferably $R_4$ is methyl;

Preferably, $R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy, aryloxy;

More preferably $R_5$ is selected from the group consisting of H, alkyl, alkoxy, halogen and fluorinated alkyl and fluorinated alkoxy;

Most preferably, $R_5$ is selected from the group consisting of chloro, bromo and trifluoromethyl;

Preferably, Y is $(CH_2)$;

Preferably, Z is O;

Preferably, W is selected from the group consisting of isoalkyl, cycloalkyl, phenyl and halogen-substituted phenyl;

More preferably, W is selected from the group consisting of isoalkyl having from 3 to 6 carbon atoms, cyclobutyl, cyclopentyl and cyclohexyl;

Most preferably, W is cyclopentyl or 3-pentyl;

The most preferred compounds of the present invention are selected from the group consisting of N-(3-{1-[5-Chloro-2-(4-chloro-benzyloxy)-benzyl]-5-methyl-1H-pyrazol-3-yl}-propionyl)-C,C,C-trifluoromethanesulfonamide, 3-{1-[5-Chloro-2-(2-ethyl-butoxy)-benzyl]-5-methyl-1H-pyrazol-3-yl}-propionic acid, 3-{1-[5-Bromo-2-(2-ethyl-butoxy)-benzyl]-5-methyl-1H-pyrazol-3-yl}-propionic acid, 3-[1-(5-Bromo-2-cyclopentylmethoxybenzyl)-5-methyl-1H-pyrazol-3-yl]-propionic acid, and, 3-[1-(2-Cyclopentylmethoxy-5-trifluoromethylbenzyl)-5-methyl-1H-pyrazol-3-yl]-propionic acid.

Figure 1:
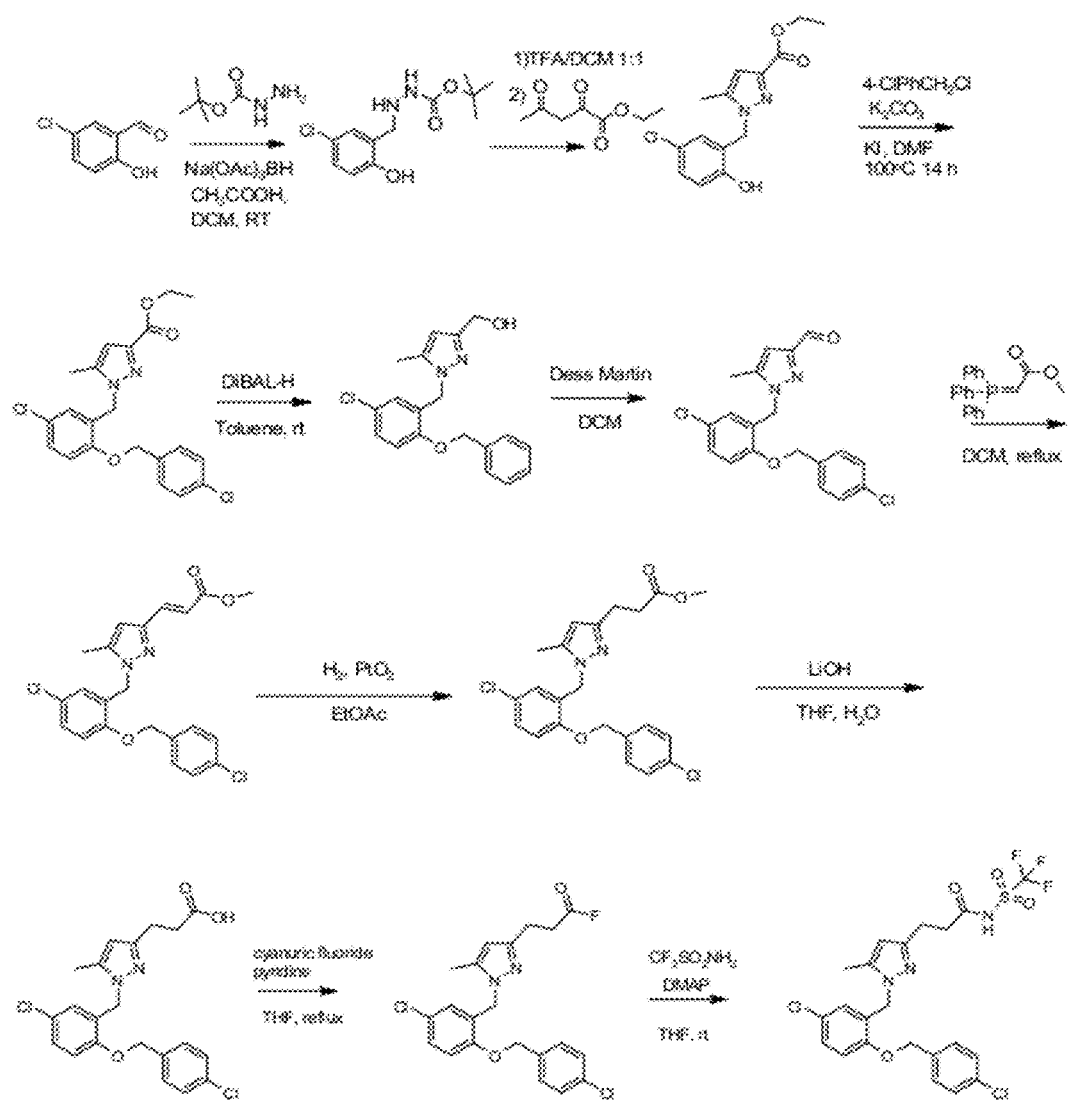
FIGS. 1 and 1a show the reaction scheme for the preparation of the compounds of this invention, wherein R is R5 and/or R6 and R2 is Z-W in the following description of the present invention.
Figure 1A:
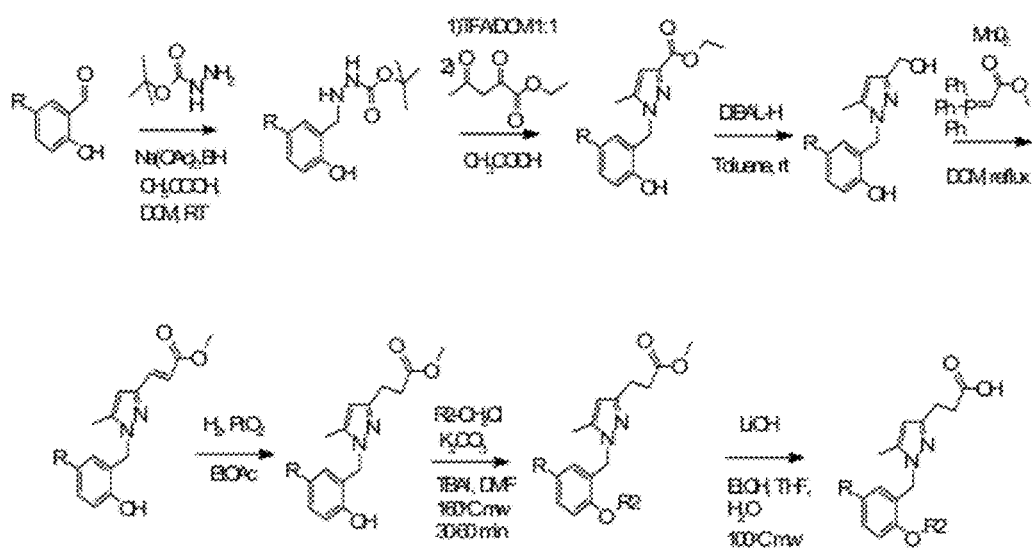

Certain of the compounds of the present invention may be prepared according to methods for preparing similar compounds as set forth in published US Patent Application 2007/0060596 which is hereby incorporated by reference. As shown in FIG. 1 preferably, certain of the preferred compounds of the present invention are prepared by reacting a {1-[5-Halo or haloalkyl-2-(4-chloro-benzyloxy or alkyloxy)-benzyl]-5-methyl-1H-pyrazole-3-carbaldehyde with trimethylphosphonoacetate to yield an (E)-3-{1-[5-Halo or haloalkyl-2-(4-chloro-benzyloxy or alkyloxy)-benzyl]-5-methyl-1H-pyrazol-3-yl}-acrylic acid methyl ester as shown in FIG. 1. Preferably, said halo is selected from the group consisting of fluoro, chloro and bromo. More preferably said haloalkyl is trifluoromethyl.

Preferably, said alkyloxy is selected from the group consisting of alkyloxy radicals wherein said alkyl is a branched chain alkyl or cycloalkyl; more preferably said alkyl is selected from the group consisting of branched chain alkyl having from 4 to 7 carbon atoms and cycloalkylmethyl wherein said cycloalkyl is cyclobutyl, cyclopentyl or cyclohexyl and most preferably said alkyl is 3-pentyl or cyclopentylmethyl.

The (E)-3-{1-[5-Halo or haloalkyl-2-(4-chloro-benzyloxy or alkyloxy)-benzyl]-5-methyl-1H-pyrazol-3-yl}-acrylic acid methyl ester is hydrogenated to yield the corresponding 3-{1-[5-Halo or haloalkyl-2-(4-chloro-benzyloxy or alkyloxy)-benzyl]-5-methyl-1H-pyrazol-3-yl}-propionic acid.

Preferably, said hydrogenation is carried out in the presence of a platinum catalyst.

The 3-{1-[5-Halo or haloalkyl-2-(4-chloro-benzyloxy or alkyloxy)-benzyl]-5-methyl-1H-pyrazol-3-yl}-propionic acid methyl ester is hydrolyzed. to yield 3-{1-[5-Halo or haloalkyl-2-(4-chloro-benzyloxy or alkyloxy)-benzyl]-5-methyl-1H-pyrazol-3-yl}-propionic acid.

The 3-{1-[5-Halo or haloalkyl-2-(4-chloro-benzyloxy or alkyloxy)-benzyl]-5-methyl-1H-pyrazol-3-yl}-propionic acid may be converted to the corresponding N-(3-{1-[5-halo or haloalkyl-2-(4-chloro-benzyloxy or alkyloxy)-benzyl]-5-methyl-1H-pyrazol-3-yl}-propionyl)-C,C,C-trifluoro-methanesulfonamide by reacting the 3-{1-[5-Halo or haloalkyl-2-(4-chloro-benzyloxy or alkyloxy)-benzyl]-5-methyl-1H-pyrazol-3-yl}-propionic acid with cyanuric fluoride in the presence of pyridine to yield 3-{1-[5-halo or haloalkyl-2-(4-chloro-benzyloxy or alkyloxy)-benzyl]-5-methyl-1H-pyrazol-3-yl}-propionyl fluoride and subsequently reacting said 3-{1-[5-halo or haloalkyl-2-(4-chloro-benzyloxy or alkyloxy)-benzyl]-5-methyl-1H-pyrazol-3-yl}-propionyl fluoride with trifluoromethanesulfonamide in the presence of DMAP to yield N-(3-{1-[5-halo or haloalkyl-2-(4-chloro-benzyloxy or alkyloxy)-benzyl]-5-methyl-1H-pyrazol-3-yl}-propionyl)-C,C,C-trifluoro-methanesulfonamide.

The following examples are intended to illustrate the present invention.

The reagents and conditions used in FIG. 1 and the Examples may be abbreviated as follows:

Ac is acetyl;

DCM is dichloromethane;

TFA is trifluoroacetic acid;

RT is room temperature;

Ph is phenyl;

DiBAL-H is diisobutylaluminumhydride;

DMF is dimethylformamide;

Et is ethyl;

THF is tetrahydrofuran;

DMAP is 4-dimethylaminopyridine;

HEPES is 4-(2-hydroxyethyl)-1-piperazineethanesulfonic acid).

Example 1

N-(3-{1-[5-CHLORO-(4-CHLORO-BENZYLOXY)-BENZYL]-5-METHYL-1H-PYRAZOL-3-YL}-PROPIONYL)-C,C,C-TRIFLUOROMETHANESULFONAMIDE, 10

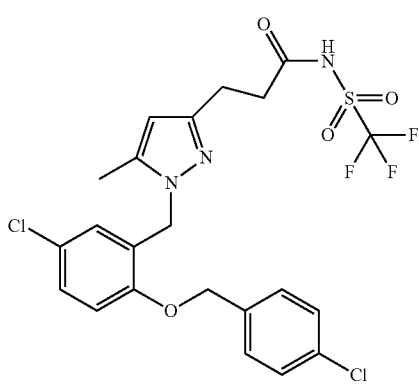 [SMILES: Cc1cc(CCC(=O)NS(=O)(=O)C(F)(F)F)nn1Cc1cc(Cl)ccc1OCc1ccc(Cl)cc1]

Step 1

N'-(5-CHLORO-2-HYDROXY-BENZYL)-HYDRAZINECARBOXYLIC ACID TERT-BUTYL ESTER 1

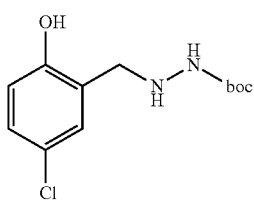

A solution of 5-chloro-2-hydroxybenzaldehyde (1.5 g, 9.3 mmol), tert-butylcarbazate (1.25 g, 9.3 mmol) and acetic acid (0.54 mL, 9.3 mmol) in CH$_2$Cl$_2$ (50 mL) was stirred under a N$_2$ atmosphere for 30 min at RT. Then sodium triacetoxyborohydride (6.20 g, 27.9 mmol) was added portion wise and the resulting mixture was stirred at RT overnight. The reaction was thoroughly quenched with 2 M HCl (15 mL) and stirred at RT for 1 h. The reaction mixture was partitioned between water (50 mL) and CH$_2$Cl$_2$ (25 mL). The aqueous layer was extracted with CH$_2$Cl$_2$ (25 mL). The combined organic layers were washed with water (2×75 mL), dried (Na$_2$SO$_4$) and evaporated to dryness to give hydrazine 1 as a white solid, 2.6 g (100%).

Step 2

1-(5-CHLORO-2-HYDROXY-BENZYL)-5-METHYL-1H-PYRAZOLE-3-CARBOXYLIC ACID ETHYL ESTER 2

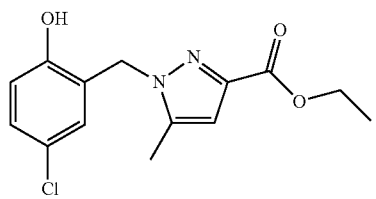 [SMILES: CCOC(=O)c1cc(C)n(Cc2cc(Cl)ccc2O)n1]

A suspension of N'-(5-Chloro-2-hydroxy-benzyl)-hydrazinecarboxylic acid tert-butyl ester 1 (9.3 mmol) in CH$_2$Cl$_2$ was treated with TFA (20 mL) and stirred at RT overnight. The volatiles were removed in vacuo. The residue was dissolved in AcOH (20 mL) and slowly added to a solution of ethyl-2,4-dioxopentanoate in AcOH (10 mL). The resulting mixture was refluxed for 1 h, allowed to cool and stirred at RT for 16 h. Precipitated 1-(5-Chloro-2-hydroxy-benzyl)-5-methyl-1H-pyrazole-3-carboxylic acid ethyl ester 2 was filtered and washed with ether. The white solid was dried overnight in a dessicator yielding 1.2 g (45%).

Step 3

1-[5-CHLORO-(4-CHLORO-BENZYLOXY)-BENZYL]-5-METHYL-1H-PYRAZOLE-3-CARBOXYLIC ACID ETHYL ESTER 3

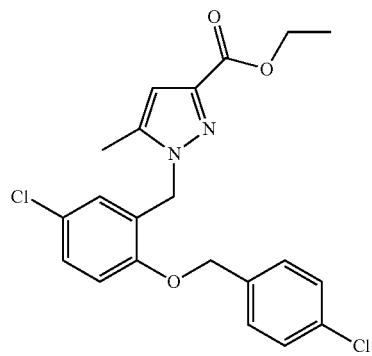 [SMILES: CCOC(=O)c1cc(C)n(Cc2cc(Cl)ccc2OCc2ccc(Cl)cc2)n1]

To a solution of 1-(5-Chloro-2-hydroxy-benzyl)-5-methyl-1H-pyrazole-3-carboxylic acid ethyl ester 2 (0.6 g, 2.0 mmol) in DMF (5 mL) were added potassium carbonate (0.84 g, 6.1 mmol), potassium iodide (0.34 g, 2.0 mmol) and 4-chlorobenzylbromide (0.38 g, 2.2 mmol). The resulting mixture was heated at 100° C. overnight. The mixture was poured into water (20 mL) and extracted with Et$_2$O (3×15 mL). The organic layers were combined, washed with brine (30 mL), dried (Na$_2$SO$_4$) and the volatiles were removed in vacuo to give 0.56 g (71%) of 1-(2-Benzyloxy-5-chloro-benzyl)-5-methyl-1H-pyrazole-3-carboxylic acid ethyl ester 3 as a white solid.

Step 4

{1-[5-CHLORO-(4-CHLORO-BENZYLOXY)-BENZYL]-5-METHYL-1H-PYRAZOL-3-YL}-METHANOL, 4

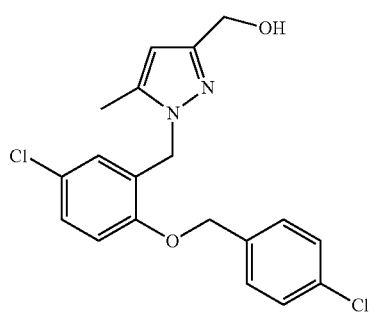 [SMILES: Cc1cc(CO)nn1Cc1cc(Cl)ccc1OCc1ccc(Cl)cc1]

To a solution of ester 3 (0.3 g, 0.72 mmol) in THF (6 mL) under $N_2$ atmosphere was added 1M LiAlH$_4$ in Et$_2$O (2.2 mL, 2.20 mmol). The resulting mixture was stirred at RT for 2 h. 2 M NaOH (2 mL) was added dropwise and the precipitate was removed by filtration. The volatiles were removed in vacuo. The residue was dissolved in EtOAc (20 mL), washed with water (2×15 mL), brine (15 mL), dried (Na$_2$SO$_4$) and evaporated to dryness to give alcohol 4 as a white solid, 0.16 g (60%).

Step 5

{1-[5-CHLORO-(4-CHLORO-BENZYLOXY)-BENZYL]-5-METHYL-1H-PYRAZOLE-3-CSR-BALDEHYDE, 5

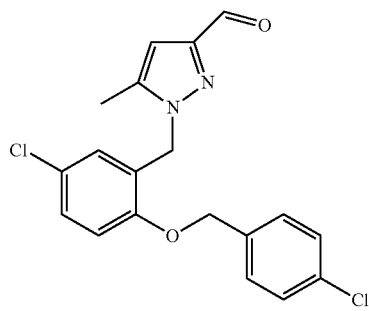 [SMILES: Cc1cc(C=O)nn1Cc1cc(Cl)ccc1OCc1ccc(Cl)cc1]

A solution of alcohol 4 (0.57 g, 1.3 mmol) and 0.5 M Dess-Martin periodinane (9.05 mL, 4.1 mmol) in CH$_2$Cl$_2$ (25 mL) was stirred under N$_2$ atmosphere at RT for 3 h. The reaction mixture was quenched with a 10% aqueous solution of Na$_2$S$_2$O$_3$ (10 mL) and extracted with more CH$_2$Cl$_2$ (10 mL). The organic layer was washed with water (10 mL), dried (Na$_2$SO$_4$) and the volatiles were removed in vacuo. The residue was purified by MPLC (5 g SiO$_2$ cartridge, eluent 70% iso-hexane—30% CH$_2$Cl$_2$) to give aldehyde 5 0.3 g (64%).

Step 6

(E)-3-{1-[5-CHLORO-(4-CHLORO-BENZYLOXY)-BENZYL]-5-METHYL-1H-PYRAZOL-3-YL}-ACRYLIC ACID METHYL ESTER, 6

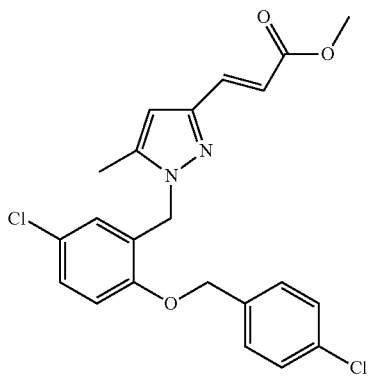 [SMILES: COC(=O)/C=C/c1cc(C)n(Cc2cc(Cl)ccc2OCc2ccc(Cl)cc2)n1]

A solution of aldehyde 5 (0.25 g, 0.65 mmol), LiCl (0.03 g, 1.21 mmol), trimethylphosphonoacetate (0.11 mL, 0.71 mmol) and DBU (0.19 mL, 1.21 mmol) in CH$_3$CN (10 mL) was stirred under a N$_2$ atmosphere at RT for 2 h. The reaction mixture was partitioned between 2 M HCl (15 mL) and EtOAc (20 mL). The organic layer was separated, washed with sat. NaHCO3 (15 mL), brine (15 mL), dried (Na$_2$SO4) and the volatiles were removed in vacuo to give a crude ester 6, 0.31 g (99%).

Step 7

3-{1-[5-CHLORO-(4-CHLORO-BENZYLOXY)-BENZYL]-5-METHYL-1H-PYRAZOL-3-YL}-PROPIONIC ACID METHYL ESTER, 7

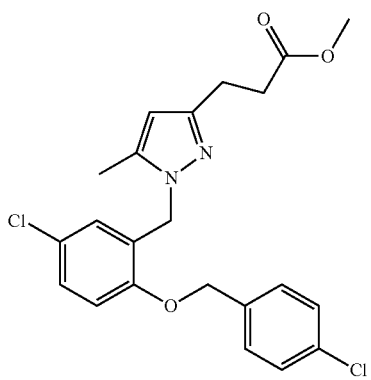 [SMILES: COC(=O)CCc1cc(C)n(Cc2cc(Cl)ccc2OCc2ccc(Cl)cc2)n1]

A suspension of unsaturated ester 6 (0.31 g, 0.65 mmol) and 5 Pt/C (0.01 g) in THF (6 mL) and MeOH (12 mL), previously purged with nitrogen, was stirred under a hydrogen atmosphere (balloon) at RT overnight. The platinum was removed by filtration through Hyflo and the filtrate was evaporated to dryness to afford the saturated ester 7, 0.31 g (99%).

Step 8

3-{1-[5-CHLORO-(4-CHLORO-BENZYLOXY)-BENZYL]-5-METHYL-1H-PYRAZOL-3-YL}-PROPIONIC ACID 8

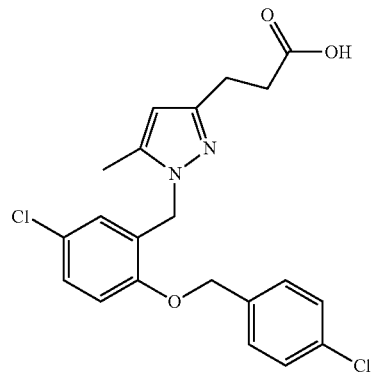 [SMILES: Cc1cc(CCC(=O)O)nn1Cc1cc(Cl)ccc1OCc1ccc(Cl)cc1]

To a solution of ester 7 (0.31 g, 0.65 mmol) in THF (5 mL) was added a solution of LiOH (0.06 g, 1.40 mmol) in water (2 mL) and the resulting mixture was stirred at RT overnight. The volatiles were removed in vacuo. The residue was diluted with water (5 mL) and acidified to pH 1 with 2 M HCl. The acid 8 was isolated by filtration as a white solid and washed with water and dried overnight over KOH in a dessicator to yield 0.09 g (34%).

Step 9

3-{1-[5-CHLORO-(4-CHLORO-BENZYLOXY)-BENZYL]-5-METHYL-1H-PYRAZOL-3-YL}-PROPIONYL FLUORIDE 9

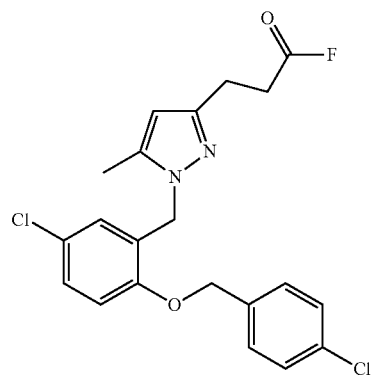 [SMILES: Cc1cc(CCC(=O)F)nn1Cc1cc(Cl)ccc1OCc1ccc(Cl)cc1]

To a solution of acid 8 (0.19 g, 0.46 mmol) in dry THF under a $N_2$ atm was added 60 μL of pyridine and 300 μL (3.4 mmol) of cyanuric fluoride. The mixture was refluxed for 2 hours, cooled to room temperature, diluted with EtOAc and washed with water and brine. After drying over $MgSO_4$, solvents were removed in vacuo to yield 0.14 g (72%) of crude acid fluoride. The crude acid fluoride was used in the next step without further purification

Step 10

N-(3-{1-[5-CHLORO-(4-CHLORO-BENZYLOXY)-BENZYL]-5-METHYL-1H-PYRAZOL-3-YL}-PROPIONYL)-C,C,C-TRIFLUORO-METHANESULFONAMIDE, 10

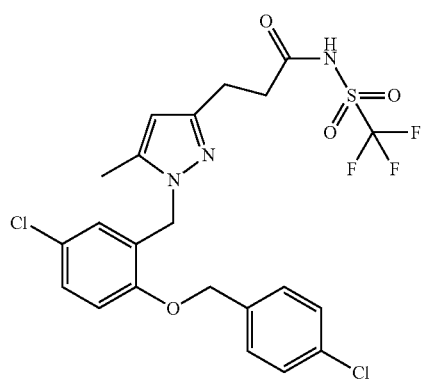 [SMILES: Cc1cc(CCC(=O)NS(=O)(=O)C(F)(F)F)nn1Cc1cc(Cl)ccc1OCc1ccc(Cl)cc1]

To a solution of acid fluoride 9 (0.14 g, 0.33 mmol) and DMAP 0.161 g (1.3 mmol) in dry DCM, trifluoromethanesulfonamide 0.147 g (0.98 mmol) was added. The mixture was stirred under a nitrogen atmosphere for 16 hours before diluting with EtOAc. The organic phase was washed with 2M HCl, followed by brine, dried over $MgSO_4$ and evaporated to dryness. The crude acyl sulphonamide 10 was purified on silica to yield 0.13 g as a white solid (72%).

Example 2

3-{1-[5-Chloro-2-(2-ethyl-butoxy)-benzyl]-5-methyl-1H-pyrazol-3-yl}-propionic acid, 17

Step 1

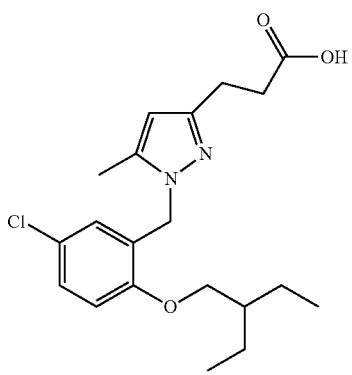 [SMILES: CCC(CC)COc1ccc(Cl)cc1Cn1nc(CCC(=O)O)cc1C]

1-(2-Benzyloxy-5-chloro-benzyl)-5-methyl-1H-pyrazole-3-carboxylic acid ethyl ester, 11

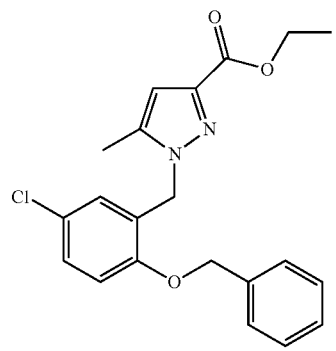 [SMILES: CCOC(=O)c1cc(C)n(Cc2cc(Cl)ccc2OCc2ccccc2)n1]

The title compound was prepared following the method in Example 1, Step 3 but substituting 4-chlorobenzyl bromide with benzyl bromide.

Step 2

[1-(2-Benzyloxy-5-chloro-benzyl)-5-methyl-1H-pyrazol-3-yl]-methanol, 12

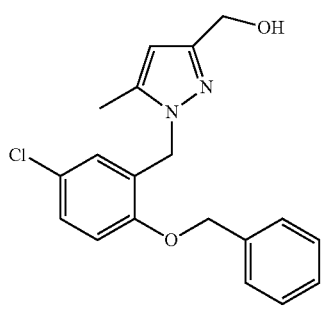 [SMILES: Cc1cc(CO)nn1Cc1cc(Cl)ccc1OCc1ccccc1]

The title compound was prepared following the method in Example 1, Step 4.

Step 3

1-(2-Benzyloxy-5-chloro-benzyl)-5-methyl-1H-pyrazole-3-carbaldehyde, 13

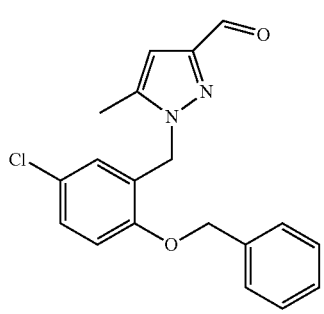 [SMILES: Cc1cc(C=O)nn1Cc1cc(Cl)ccc1OCc1ccccc1]

The title compound was prepared following the method in Example 1, Step 5.

Step 4

(E)-3-[1-(2-Benzyloxy-5-chloro-benzyl)-5-methyl-1H-pyrazol-3-yl]-acrylic acid methyl ester, 14

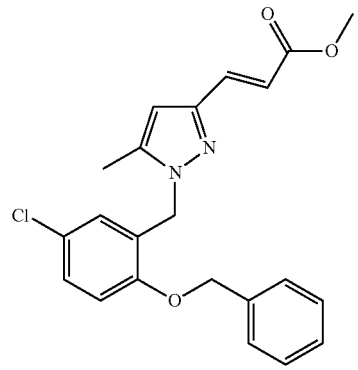 [SMILES: COC(=O)/C=C/c1cc(C)n(Cc2cc(Cl)ccc2OCc2ccccc2)n1]

To a stirred solution of aldehyde 13, (1 g, 2.9 mmol) in THF was added (methoxycarbonylmethylene)triphenylphosphorane, 2 g (6 mmol). The mixture was stirred at room temperature for 70 hours. The mixture was diluted with EtOAc and the organic phase was washed with 2M HCl, saturated $NaHCO_3$ and brine, dried over $MgSO_4$ and evaporated in vacuo. The crude unsaturated ester 14 was purified on silica to yield 1.2 g as a white solid (99%).

Step 5

3-[1-(5-Chloro-2-hydroxy-benzyl)-5-methyl-1H-pyrazol-3-yl]-propionic acid methyl ester, 15

A stirred solution of unsaturated ester 14, (1.2 g, 2.9 mmol) and $PtO_2$, 0.12 g in acetic acid (25 mL) and conc. HCl (5 mL) was hydrogenated at room temperature for 16 hours. The catalyst was removed by filtration through Hyflo and the filtrate was evaporated to dryness to afford the saturated ester 15, 0.8 g (90%).

Step 6

3-{1-[5-Chloro-2-(2-ethyl-butoxy)-benzyl]-5-methyl-1H-pyrazol-3-yl}-propionic acid methyl ester 16

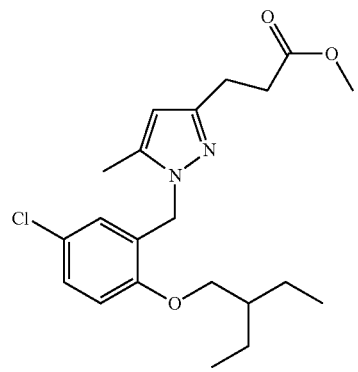 [SMILES: CCC(CC)COc1ccc(Cl)cc1Cn1nc(CCC(=O)OC)cc1C]

To a solution of 3-{1-[5-Chloro-2-(2-ethyl-butoxy)-benzyl]-5-methyl-1H-pyrazol-3-yl}-propionic acid methyl ester 15 (0.2 g, 0.63 mmol) in DMF (5 mL) were added potassium carbonate 0.15 g (1.26 mmol), tetrabutylammonium iodide 0.03 g and 3-chloromethylpentane 0.15 g (1.26 mmol). The resulting mixture was heated at 150° C. in a microwave reactor. The mixture was poured into water and extracted with EtOAc. The organic layers were combined, washed with brine (30 mL), dried (MgSO$_4$) and the volatiles were removed in vacuo to give 0.21 g (84%) of the methyl ester 16 as a white solid.

Step 7

3-{1-[5-Chloro-2-(2-ethyl-butoxy)-benzyl]-5-methyl-1H-pyrazol-3-yl}-propionic acid, 17

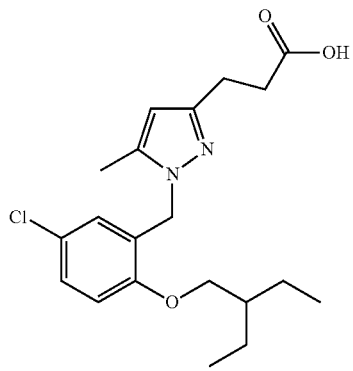 [SMILES: CCC(CC)COc1ccc(Cl)cc1Cn1nc(CCC(=O)O)cc1C]

The title compound was prepared following the method in Example 1, Step 8.

Example 3

3-{1-[5-Bromo-2-(2-ethyl-butoxy)-benzyl]-5-methyl-1H-pyrazol-3-yl}-propionic acid, 18

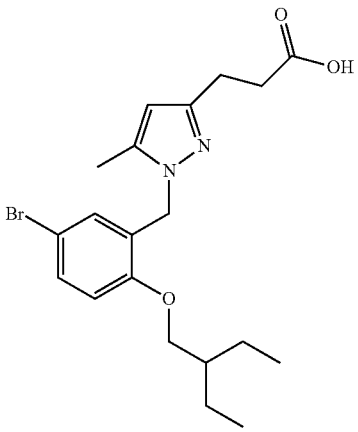 [SMILES: CCC(CC)COc1ccc(Br)cc1Cn1nc(CCC(=O)O)cc1C]

The title compound was prepared following the methods described in example 1 and example 2 but starting initially (example 1 step 1) with 5-bromo-2-hydroxybenzaldehyde.

Example 3(a)

3-{1-[5-Chloro-2-(2-ethyl-butoxy)-benzyl]-5-methyl-1H-pyrazol-3-yl}-propionic acid, is prepared in a similar manner starting initially with 5-chloro-2-hydroxybenzaldehyde.

Example 4

3-[1-(5-Bromo-2-cyclopentylmethoxybenzyl)-5-methyl-1H-pyrazol-3-yl]-propionic acid 19

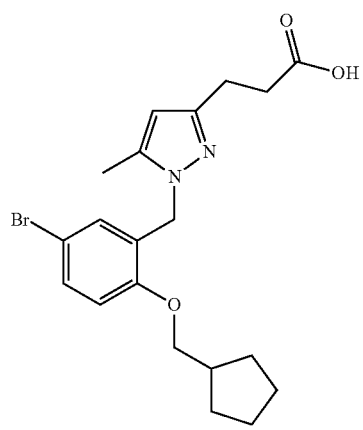 [SMILES: Cc1cc(CCC(=O)O)nn1Cc1cc(Br)ccc1OCC1CCCC1]

The title compound was prepared following the methods described in example 1 and example 2 but starting initially (example 1 step 1) with 5-bromo-2-hydroxybenzaldehyde and replacing 3-chloromethylpentane in example 2 step 6 with chloromethylcyclopentane.

Example 4(a)

3-[1-(5-Chloro-2-cyclopentylmethoxybenzyl)-5-methyl-1H-pyrazol-3-yl]-propionic acid is also prepared following the methods described in example 1 and example 2 but starting initially (example 1 step 1) with 5-chloro-2-hydroxybenzaldehyde and replacing 3-chloromethylpentane in example 2 step 6 with chloromethylcyclopentane.

Example 5

3-[1-(2-Cyclopentylmethoxy-5-trifluoromethylbenzyl)-5-methyl-1H-pyrazol-3-yl]-propionic acid, 19

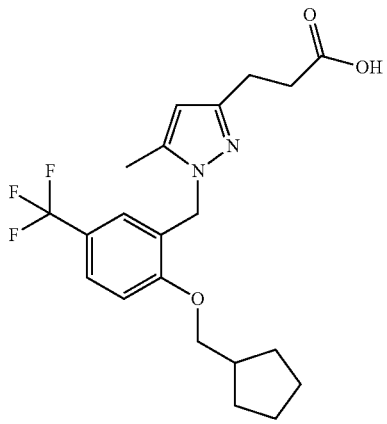 [SMILES: Cc1cc(CCC(=O)O)nn1Cc1cc(C(F)(F)F)ccc1OCC1CCCC1]

The title compound was prepared following the methods described in example 1 and example 2 but starting initially (example 1 step 1) with 5-trifluoromethyl-2-hydroxybenzaldehyde and replacing 3-chloromethylpentane in example 2 step 6 with chloromethylcyclopentane.

The present invention provides a method of making 3-{1-[5-Halo or haloalkyl-2-(4-chloro-benzyloxy or 4-chloro-alkyloxy)-benzyl]-5-methyl-1H-pyrazol-3-yl}-propionic acid which comprises hydrolyzing a 3-{1-[5-Halo or haloalkyl-2-(4-chloro-benzyloxy or 4-chloro-alkyloxy)-benzyl]-5-methyl-1H-pyrazol-3-yl}-propionic acid methyl ester, to yield 3-{1-[5-Halo or haloalkyl-2-(4-chloro-benzyloxy or 4-chloro-alkyloxy)-benzyl]-5-methyl-1H-pyrazol-3-yl}-propionic acid, wherein said halo is selected from the group consisting of fluoro, chloro and bromo, e.g. said haloalkyl may be trifluoromethyl.

Preferably, said alkyloxy may be selected from the group consisting of alkyloxy wherein said alkyl comprises from 4 to 7 carbon atoms Preferably, said alkyl may be selected from the group consisting of 3-pentyl and cyclopentylmethyl.

Said 3-{1-[5-Halo or haloalkyl-2-(4-chloro-benzyloxy or 4-chloro-alkyloxy)-benzyl]-5-methyl-1H-pyrazol-3-yl}-propionic acid may be prepared by hydrogenating the corresponding (E)-3-{1-[5-Halo or haloalkyl-2-(4-chloro-benzyloxy or 4-chloro-alkyloxy)-benzyl]-5-methyl-1H-pyrazol-3-yl}-acrylic acid methyl ester to yield 3-{1-[5-Halo or haloalkyl-2-(4-chloro-benzyloxy or 4-chloro-alkyloxy)-benzyl]-5-methyl-1H-pyrazol-3-yl}-propionic acid, e.g. said hydrogenation may be carried out in the presence of a platinum catalyst.

Said (E)-3-{1-[5-Halo or haloalkyl-2-(4-chloro-benzyloxy or 4-chloro-alkyloxy)-benzyl]-5-methyl-1H-pyrazol-3-yl}-acrylic acid methyl ester may be prepared by reacting trimethylphosphonoacetate with the corresponding {1-[5-Halo or haloalkyl-2-(4-chloro-benzyloxy or 4-chloro-alkyloxy)-benzyl]-5-methyl-1H-pyrazole-3-carbaldehyde to yield said (E)-3-{1-[5-Halo or haloalkyl-2-(4-chloro-benzyloxy or 4-chloro-alkyloxy)-benzyl]-5-methyl-1H-pyrazol-3-yl}-acrylic acid methyl ester.

As can be understood from the above examples, the present invention also provides a method of making N-(3-{1-[5-halo or haloalkyl-2-(4-chloro-benzyloxy or 4-chloro-alkyloxy)-benzyl]-5-methyl-1H-pyrazol-3-yl}-propionyl)-C,C,C-trifluoro-methanesulfonamide comprising the step of (a) reacting the corresponding. 3-{1-[5-Halo or haloalkyl-2-(4-chloro-benzyloxy or 4-chloro-alkyloxy)-benzyl]-5-methyl-1H-pyrazol-3-yl}-propionic acid with cyanuric fluoride to yield 3-{1-[5-halo or haloalkyl-2-(4-chloro-benzyloxy or 4-chloro-alkyloxy)-benzyl]-5-methyl-1H-pyrazol-3-yl}-propionyl fluoride and (b) reacting said 0.3-{1-[5-halo or haloalkyl-2-(4-chloro-benzyloxy or 4-chloro-alkyloxy)-benzyl]-5-methyl-1H-pyrazol-3-yl}-propionyl fluoride with trifluoromethanesulfonamide to yield N-(3-{1-[5-halo or haloalkyl-2-(4-chloro-benzyloxy or 4-chloro-alkyloxy)-benzyl]-5-methyl-1H-pyrazol-3-yl}-propionyl)-C,C,C-trifluoro-methanesulfonamide.

Preferably, said step (a) is carried out in the presence of pyridine and said step (b) is carried out in the presence of DMAP.

The above compounds were tested for PG antagonist activity as follows using human recombinant prostanoid receptor ($DP_1$, $EP_{1-4}$, FP, IP and TP) stable cell lines:

In order to measure the response of $G_s$ and $G_i$ coupled prostanoid receptors as a $Ca^{2+}$ signal, chimeric G protein cDNAs were used. Stable cell lines over-expressing human prostanoid $DP_1$, $EP_{1-4}$, FP, IP, and TP receptors were established as follows:

Briefly, human prostanoid $DP_1$, $EP_2$, and $EP_4$ receptor cDNAs were co-transfected with chimeric $G_{qs}$ cDNA containing a haemagglutanin (HA) epitope; human prostanoid $EP_3$ receptors were co-transfected with chimeric $G_{qi}$-HA; human $EP_1$, FP, IP, and TP receptor cDNAs were expressed with no exogenous G-proteins. $G_{qs}$ and $G_{qi}$ chimeric cDNAs (Molecular Devices, Sunnyvale, Calif., U.S.A.), as well as cDNAs of prostanoid receptors, were cloned into a $pCEP_4$ vector with a hygromycin B selection marker. Transfection into HEK-293 EBNA (Epstein-Barr virus nuclear antigen) cells was achieved by the FuGENE 6 transfection Reagent (Roche Applied Science, Indianapolis, Ind., USA). Stable transfectants were selected according to hygromycin resistance. Because $G_{qs}$ and $G_{qi}$ contained an HA epitope, G-protein expression was detected by Western blotting analysis using anti-mouse HA monoclonal antibody and horseradish peroxidase (HRP)-conjugated secondary antibody, while functional expression of prostanoid receptors was detected by FLIPR screening (Matias et al., 2004). These stable cell lines were validated using previously published antagonists at 10 µM against serial dilutions of standard agonists by FLIPR functional assays for $Ca^{2+}$ Signaling (as described below).

$Ca^{2+}$ signaling studies were performed using a FLIPR TETRA system (Molecular Devices, Sunnyvale, Calif., USA) in the 384-format. This is a high-throughput instrument for cell-based assays to monitor $Ca^{2+}$ signaling associated with GPCRs and ion channels. Cells were seeded at a density of $5 \times 10^4$ cells/well in BioCoat poly-D-lysine coated, black wall, clear bottom 384-well plates (BD Biosciences, Franklin lakes, NJ, USA) and allowed to attach overnight in an incubator at 37° C. The cells were then washed twice with HBSS-HEPES buffer (Hanks' balanced salt solution without bicarbonate and phenol red, 20 mM HEPES, pH 7.4) using an ELx405 Select CW Microplate Washer (BioTek, Winooski, Vt., USA). After 60 min of dye-loading in the dark using the $Ca^{2+}$-sensitive dye Fluo-4AM (Invitrogen, Carlsbad, Calif., USA), at a final concentration of $2 \times 10^{-6} M$, the plates were washed 4 times with HBSS-HEPES buffer to remove excess dye and leaving 50 µl of buffer in each well. The plates were then placed in the FLIPR TETRA instrument and allowed to equilibrate at 37° C. AGN-211377 was added in a 25 μl volume to each well to give final concentrations of 0.1 μM, 0.3 μM, 1 μM, 3 μM, 10 μM, and 30 μM; or 0.067 μM, 0.1 μM, 0.2 μM, 0.67 μM, and 1 μM for cells over-expressing TP receptors. After 4.5 minutes, a 7-point serial dilution of the standard agonist for the corresponding receptor, in a 25 μl volume was injected at the final concentrations from $10^{-11}$M to $10^{-5}$M 10-fold serial dilution increments for cells expressing human recombinant $DP_1$, $EP_1$, $EP_2$, $EP_3$, $EP_4$, FP, and IP receptors. The dose range for the standard agonist for human recombinant TP receptors was from $10^{-12}$M to $10^{-6}$M. HBSS-HEPES buffer was used as the negative control for the standard agonists. Cells were excited with LED (light emitting diode) excitation at 470-495 nm and emission was measured through an emission filter at 515-575 nm. Assay plates were read for 3.5 minutes using the FLIPR$^{TETRA}$. The peak increase in fluorescence intensity was recorded for each well. On each plate, negative controls, dose response of positive controls, and co-treatments of antagonist-agonist for each dose were in triplicates. Standard agonists were as follows: DP=BW 245C, $EP_1$-$EP_4$=$PGE_2$, FP=17-phenyl-$PGF_{2\alpha}$, IP=Cicaprost, and TP=U-46619. The peak fluorescence change in each well containing drug was expressed relative to vehicle controls with the standard agonist at $10^{-6}$M (the positive control). To obtain concentration-response curves, compounds were tested in triplicate in each plate over the desired concentration range.

$Ca^{2+}$ Signal Studies on Human Recombinant Prostanoid Receptor $DP_2$

FLIPR functional assays were conducted at Millipore to monitor the activity anti-asthmatic against human $DP_2$ receptors stably expressed in the Chem-5 proprietary host cell line generated by Millipore. Prior to standard agonist addition, the compounds were spotted at 10 μM along with vehicle control (1% Ethanol in HBSS-HEPES buffer) across the assay wells. The assay plate was incubated at room temperature for 10 minutes in the dark. Then an 8-point serial dilution dose response from $10^{-12}$M to $10^{-5}$M of the standard agonist $PGD_2$ was performed. Assay plates were read for 90 seconds using the FLIPR$^{TETRA}$. The fluorescence measurements were collected to calculate $IC_{50}$ values. The assays were done at least 3 times to give n=3.

Data Processing

All plates were subjected to appropriate baseline corrections. Maximum fluorescence values were exported. The raw data of n=1 was first processed by Activity Base using nonlinear regression curve fit to calculate the percentage activity of each data point relative to the positive control (=$10^{-6}$M of the standard agonist). Then n=3 of this data were exported to GraphPad Prism 4 to calculate the average $EC_{50}$ of the standard agonist, and the $IC_{50}$ (the concentration of the antagonist required to inhibit half the standard agonist activity) were calculated using nonlinear regression curve fit, with constraints of bottom constant equal to 0 and top constant equal to 100. Calculation of Kb=[Antagonist Concentration]/($IC_{50}$/$EC_{50}$−1). When no antagonism was detected or when Kb≧10,000 nM, the antagonist is defined as not active (NA).

The results of the above testing are reported in TABLE 1, below.

TABLE 1

| Example No. | FP | $DP_1$ | $EP_1$ | $EP_2$ | $EP_3$ | $EP_4$ | IP | TP |
|---|---|---|---|---|---|---|---|---|
| 1 | 140 | 280 | 22 | 3100 | 1400 | 150 | 620 | 12 |
| 4a | 110 | 280 | 80 | 4500 | NA | 180 | 1200 | 3 |
| 5 | 63 | 220 | 24 | 3400 | NA | 240 | 6800 | 7 |
| 3a | 180 | 220 | 71 | 2900 | 7100 | 68 | 1100 | 5 |
| 4 | 75 | 240 | 24 | 1200 | 7800 | 120 | 1600 | 30 |
| 3 | 75 | 140 | 40 | 2300 | NA | 85 | 1600 | 9 |

(FLIPR) $K_b$ (nM), NA=inactive

As shown in TABLE 1, the preferred compounds of this invention are pan antagonists having activity at the FP, DP, $EP_1$, $EP_4$ and TP receptors, but are inactive at the $EP_2$ and $EP_3$ receptors. Thus, these compounds have a biological selectivity profile making them useful in treating diseases and conditions which are mediated by the $EP_2$ and/or $EP_3$ receptors, without the side effects mediated by the FP, DP, $EP_1$, $EP_4$ and TP receptors.

Thus, the compounds of this invention compound may be administered to treat DP1, FP, EP1, TP and/or EP4 receptor mediated diseases or conditions.

For example, said condition or disease may be related to inflammation, or said DP1, FP, EP1, TP and/or EP4 receptor mediated condition or disease may be selected from the group consisting of allergic conditions, asthma, allergic asthma, allergic rhinitis, uveitis and related disorders, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, fertility disorders, gangrene, glaucoma, hyperpyrexia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, rheumatoid arthritis, pain, perennial rhinitis, pulmonary congestion, pulmonary hypotension, Raynaud's disease, rejection in organ transplant and by-pass surgery, respiratory conditions, hirsutism, rhinorrhea, shock, sleep disorders, and sleep-wake cycle disorders.

Said compound may be administered as a surgical adjunct in ophthalmology for cataract removal and artificial lens insertion, ocular implant procedures, photorefractive radial keratotomy and other ophthalmogical laser procedures or as a surgical adjunct in a procedure involving skin incisions, relief of pain and inflammation and scar formation/keloids postsurgery, for treating sports injuries and general aches and pains in muscles and joints.

Preferably, said $DP_1$, FP, $EP_1$, TP, and/or $EP_4$ receptor mediated condition or disease is an $EP_1$ and/or $EP_4$ receptor mediated condition or disease.

Preferably, said $DP_1$, FP, $EP_1$, TP and/or $EP_4$ receptor mediated condition or disease is an allergic condition, e.g. an dermatological allergy, or an ocular allergy, or a respiratory allergy, e.g. nasal congestion, rhinitis, and asthma.

Said condition or disease may be related to pain.

Said condition or disease may be selected from the group consisting of arthritis, migraine, and headache.

Said condition or disease may be associated with the gastrointestinal tract, wherein said condition or disease may be peptic ulcer, heartburn, reflux esophagitis, erosive esophagitis, non-ulcer dyspepsia, infection by *Helicobacter pylori*, alrynitis, and irritable bowel syndrome.

Said condition or disease may be selected from the group consisting of hyperalgesia and allodynia, or said condition or disease may be related to mucus secretion, wherein said mucus secretion is gastrointestinal, or occurs in the nose, sinuses, throat, or lungs.

Said condition or disease is related to abdominal cramping, e.g. said condition or disease may be irritable bowel syndrome.

Said condition or disease may be a bleeding disorder, or a sleep disorder, or mastocytosis.

Said condition or disease may be associated with elevated body temperature, or ocular hypertension and glaucoma, or ocular hypotension.

Said condition may relate to surgical produres to treat pain, inflammation and other unwanted sequelae wherein said surgical procedure includes incision, laser surgery or implantation.

The present invention also relates to a method of treating inflammation resulting from inflammatory diseases characterized by monocytic infiltration caused by the secretion of cytokines and/or chemokines by administration, to a patient in need of said treatment, of a pharmaceutical composition comprising a compound of the present invention The current finding that the compounds of this invention are effective in attenuating the production of TNF family cytokines (TNFα), and the classical interleukin-1 (IL-1) family cytokines is especially important. These cytokines exert a broad spectrum of biological and pathological effects. They play key roles in inflammation and RA pathogenesis by stimulating the release of multiple proinflammatory cytokines, including themselves, through the NFκB signaling pathway. Although alleviating the symptoms of RA in 50-65% of patients, a TNFα antibody is very expensive to use compared to chemically synthesized small molecules, inconvenient to administer usually requiring injections, and has been linked to tuberculosis, lymphoma, and other adverse effects. Unlike a TNFα antibody that totally eliminates all circulating TNFα in the system; the compounds of this invention only attenuate the production of TNFα by inhibiting proinflammatory PG receptors. Therefore the adverse effects associated with a TNFα antibody in elevating infectious and cancerous tendency is less likely.

Proinflammatory elements TNF, RANTES, and MCP-1 are involved in the cascade of events in the early and late stages of atherosclerosis. Plasma MCP-1 levels have been linked to cardiovascular disease risk factors in clinical studies. Platelet activation leads to the release of MIP-1α, RANTES, and IL-8, which attract leukocytes and further activate other platelets. These evidences provide a direct linkage between homeostasis, infection, and inflammation and the development of atherosclerosis. The compounds of this invention are able to target multiple biomarkers of inflammation, thrombosis, and atherothrombosis simultaneously, which may confer pharmaceutical potential on the compounds of this invention in treating atherosclerosis and atherothrombosis. As a result, the compounds of this invention are unlikely to be associated with cardiovascular liability as in the case of the COXIBs, conversely it may even have a beneficial effect on cardiovascular function.

In summary, because of their ability to suppress the synthesis of some key proinflammatory cytokines/chemokines IL-8, MCP-1, MDC, RANTES, and TNFα, the compounds of the present invention are not only at least as effective as COXIBs and NSAIDs in RA treatment, but also are a safer therapy in RA treatment. They are also a potential therapy for cardiovascular diseases.

The compounds of this invention treat or prevent inflammation at least in part by the decreasing the amount of the secretion of certain cytokines and/or chemokines that result from the exposure of the patient to a stimulant.

In particular, the secretion of VEGF, MIP-1β, IL-8, MCP-1, , , , , MDC, and RANTES is reduced in those instances where said secretions are triggered by lipopolysaccharides (LPS) and or TNFα.

Interleukin-8 (IL-8): functions as a potent chemoattractantsand activator of neutrophils, IL-8 is produced in response to stimulation with either IL-1 or TNFα. IL-8 not only accounts for a significant proportion of the chemotactic activity for neutrophils in rheumatoid arthritis (RA) synovial fluids, but also is a potent angiogenic factor in the RA synovium.

Monocyte chemoattractant protein-1 (MCP-1, or CCL-2): is not only believed to play a role in inflammatory diseases characterized by monocytic infiltration, such as RA rheumatoid arthritus, psoriasis, and atherosclerosis, but is also implicated in other diseases, such as atopic dermatitis, renal disease, pleurisy, allergy and asthma, colitis, endometriosis, polymyositis and dermatomyositis, uveitis, restenosis, brain inflammation and obesity. MCP-1 also controls leukocyte trafficking in vascular cells involved in diabetes and diabetes-induced atherosclerosis. MCP-1 antibodies are potential therapeutic agents for treating MCP-1/CCR2-mediated multiple inflammatory diseases.

Tumor necrosis factor α (TNFα): mainly secreted by macrophages and recognized for its importance in activating the cytokine cascade. TNFα stimulates the production of proinflammatory cytokines/chemokines, collagenases, metalloproteinases, and other inflammatory mediators; activates endothelial cells and neutrophils; promotes T- and B-cell growth, as well as stimulating bone resorption. The TNFα antibody infliximab not only decreases the production of local and systemic proinflammatory cytokines/chemokines, but also reduces serum MMP-3 production, nitric oxide synthase activity, VEGF release, and angiogenesis in inflamed joints.

Macrophage-derived chemokine (MDC) induces chemotaxis for monocyte-derived dendritic cells, activated T cells and natural killer (NK) cells (Ho et al., 2003). Highly expressed by the three major cell types involved in allergic inflammation: eosinophils, basophils, and Th2 lymphocytes (Garcia et al., 2005), as well as highly expressed in atopic dermatitis (Pivarcsi et al., 2005), MDC plays a role in inflammatory diseases such as allergic asthma and atopic dermatitis (Ho et al., 2003). Significantly enhanced in keratinocytes of patients with atopic dermatitis, MDC could be a candidate therapeutic target for inflammatory skin disease such as atopic dermatitis (Qi et al., 2009). MDC is also implicated in disease activity of RA. After combination treatment with the disease-modifying anti-rheumatic drugs leflunomide and methotrexate in RA patients, plasma MCP-1 and MDC concentrations were significantly lower, and so was the recruitment of inflammatory cells into the sites of inflammation (Ho et al., 2003). Moreover, MDC also amplify platelet activation and has been associated with the pathogenesis of atherosclerotic disease including thrombosis (Gleissner et al., 2008).

Regulated on Activation, Normal T Cell Expressed and Secreted (RANTES) is a chemoattractant for blood monocytes, memory T-helper cells and eosinophils, and plays an active role in recruiting leukocytes into inflammatory sites. It also stimulates the release of histamine from basophils, activates eosinophils and causes hypodense eosinophils, which is associated with diseases such as asthma and allergic rhinitis. RANTES receptor CCR5 is also expressed on cells involved in atherosclerosis (e.g. monocytes/macrophages, T lymphocytes, or Th1-type cells), and is specialized in mediating RANTES-triggered atherosclerotic plaque formation (Zemecke et al., 2008). Like MCP-1, stimulation with RANTES enhances production of IL-6 and IL-8 in RA fibroblast-like synovial cells; elevated MMP-3 production by chondrocytes, and inhibited proteoglycan synthesis and enhanced proteoglycan release from the chondrocytes (Iwamoto et al., 2008). Both MCP-1 and RANTES were found to play an important role in allergic lung inflammation, lung leukocyte infiltration, bronchial hyper-responsiveness, and the recruitment of eosinophils in the pathogenesis of asthma (Conti et al., 2001). Similar to MCP-1, RANTES also enhances the inflammatory response within the nervous system, which plays an apparent role in the pathogenesis of multiple sclerosis (Conti et al., 2001). Inhibitors for RANTES may provide clinical benefits in treating inflammation, CNS disorders, parasitic disease, cancer, autoimmune and heart diseases (Castellani et al., 2007).

While the use of the compounds of this invention are shown to decrease the secretion of the above cytokines in FIGS. 2 through 9, it is believed that the compounds of this invention are effective to decrease the secretion of ENA-7, PAI-1, CD-10, G-CSF, GM-CSF, IL-1α, and IL-18, as well.

The compounds of this invention are also tested for efficacy in treating uveitis as described below.

Arachidonate Induced Uveitis

The rational for this protocol is to use arachidonate to directly produce ocular anterior segment uveitis, as opposed to using lipopolysaccharide (LPS) to indirectly release arachidonic acid.

Induction of Uveitis:

Conscious male or female Dutch-belted pigmented rabbits weighing 2.5-3 kg were used for all in vivo slit lamp studies. Four animals were employed per test group. The right eye of each animal receiving 35 µl of topically administered test and the contralateral left eye of each animal receiving 35 µl of topically administered vehicle (t=0 minutes), followed 30 minutes later by treatment with 35 µl of 0.5% sodium arachidonate onto the surface of both eyes (t=30 minutes). Both eyes were examined by slit lamp 60 minutes following sodium arachdionate challenge (t=90 minutes) at 16× magnification under both white light and blue light illumination at an approximate angle of 45° through 1 mm and 5 mm slit widths.

Measurement of Anterior Chamber Leukocyte Infiltration:

Anterior chamber leukocyte infiltration was measured using a numerical scoring system to estimate cell number per field defined by a 5 mm slit width: 0=no cells per field (no response); 1=1-10 cells per field (mild); 2=11-20 cells per field (moderate); 3=26-50 cells per field (severe); 4=>50 cells per filed (florid). Results are reported as the mean score value±S.E.M.

The results are shown in FIG. 12. In FIG. 12 the compounds of Example 3 and 3a were tested at concentrations of 0.1, 0.3 and 1% and a dose dependent response was observed for each compound.

The compounds of this invention were tested according to the method described in "Characterization of Receptor Subtypes Involved in Prostanoid-Induced Conjunctival Pruritis and Their Role in Mediating Conjunctival Itching", Vol. 279, No. 1, (JPET)279, 137-142' 1996 for their efficacy in alleviating itch. The results are reported in FIGS. 10 and 11. The results in both experiments showed a significantly lower number of itch-scratch episodes with the use of the compounds of FIGS. 3 and 3(a) thereby indicating that the compounds of this invention are useful in treating allergic conjunctivitis.

The compounds of FIGS. 3 and 3(a) were tested for mutagenicity by means of the Ames Test using Strains TA 98 and TA 100. The results were negative for both compounds.

Finally, said condition that may be treated with the compounds of this invention may be related to pain and inflammation and post-surgical scar and keloid formation.

In view of the various diseases and conditions that may be treated with the compositions of this invention there is provided a pharmaceutical product comprising a compound having the following formula

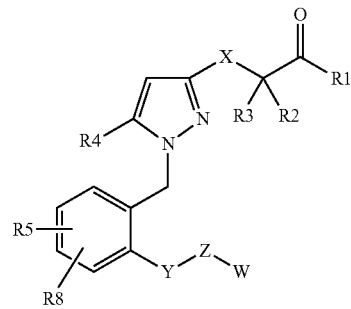

Wherein $R_1$ is selected from the group consisting of $OR_7$, $N(R_7)_2$, and $N(R_7)SO_2R_7$ wherein $R_7$ is selected from the group consisting of H, alkyl and aryl, wherein said alkyl and aryl may be substituted with fluoro;
$R_2$ is selected from the group consisting of H and alkyl;
$R_3$ is selected from the group consisting of H and alkyl; wherein $R_2$ and $R_3$, individually or together, can form a cycloalkyl ring;
X is $(CH_2)_n$ wherein n is 0 or an integer of from 1 to 3; provided however that when n is 0 or 1, $R_1$ is not $OR_7$. or $NR_2$;
$R_4$ is selected from the group consisting of H, alkyl and fluoroalkyl;
$R_5$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy or aryloxy;
$R_6$ is selected from the group consisting of H, hydroxy, alkyl, aryl, alkoxy, aryloxy, halogen, nitro, amino, cyano and hydroxy, halogen, nitro, amino and cyano-substituted alkyl, aryl, alkoxy and aryloxy;
Z is $(CH_2)_m$ wherein m is 0 or an integer of from 1 to 3:
Y is selected from the group consisting of O, S, SO, $SO_2$ and $(CH_2)_p$, wherein p is 0 or an integer of from 1 to 3; and
W is selected from the group consisting of alkyl and aryl
or a pharmaceutically acceptable salt or a prodrug thereof, wherein said product is packaged and labeled for the treatment or prevention of a disease or condition selected from the group consisting of uveitis, allergic conditions, asthma, allergic asthma, allergic rhinitis, atherosclerosis, blood coagulation disorders, bone disorders, cancer, cellular neoplastic transformations, chronic obstructive pulmonary diseases and other forms of lung inflammation, congestive heart failure, diabetic retinopathy, diseases or conditions requiring a treatment of anti-coagulation, diseases requiring control of bone formation and resorption, fertility disorders, hyperpyrexia, gangrene, glaucoma, hypothermia, immune and autoimmune diseases, inflammatory conditions, metastic tumor growth, migraine, mucus secretion disorders, nasal congestion, nasal inflammation, occlusive vascular diseases, ocular hypertension, ocular hypotension, osteoporosis, pain, perennial rhinitis, pulmonary congestion, pulmonary hypotension, Raynaud's disease, rejection in organ transplant and by-pass surgery, respiratory conditions, rheumatoid arthritis, rhinorrhea, shock, sleep disorders, sleep-wake cycle disorders, sports injuries, muscle aches and pains, and surgical adjunct for minimizing pain, inflammation and scar/keloid formation.

Those skilled in the art will readily understand that for administration the compounds disclosed herein can be admixed with pharmaceutically acceptable excipients which, per se, are well known in the art. Specifically, a drug to be administered systemically, it may be formulated as a powder, pill, tablet or the like, or as a solution, emulsion, suspension, aerosol, syrup or elixir suitable for oral or parenteral administration or inhalation.

For solid dosage forms, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate.

The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distcarate may be employed. They may also be coated by the technique described in the U.S. Pat. Nos. 4,256,108; 4,166, 452; and 4,265,874 to form osmotic therapeutic tablets for control release. Liquid pharmaceutically administrable dosage forms can, for example, comprise a solution or suspension of one or more of the compounds of the present invention and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectable formulations can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds of the present invention, administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. The therapeutically effective dosage of the presently useful compound or compounds is preferably in the range of about 0.5 ng/kg/day or about 1 ng/kg/day to about 100 mg/kg/day.

For ophthalmic application, solutions are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

Similarly, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edentate disodium, although other chelating agents may also be used in place or in conjunction with it.

For topical use, creams, ointments, gels, solutions or suspensions, etc., containing the compound of the present invention are employed. Topical formulations may generally be comprised of a pharmaceutical carrier, cosolvent, emulsifier, penetration enhancer, preservative system, and emollient.

The actual dose of the compounds of the present invention depends on the specific compound, and on the condition to be treated; the selection of the appropriate dose is well within the knowledge of the skilled artisan.

The present invention is not to be limited in scope by the exemplified embodiments, which are only intended as illustrations of specific aspects of the invention. Various modifications of the invention, in addition to those disclosed herein, will be apparent to those skilled in the art by a careful reading of the specification, including the claims, as originally filed. It is intended that all such modifications will fall within the scope of the appended claims

What is claimed is:
1. A compound having the following formula

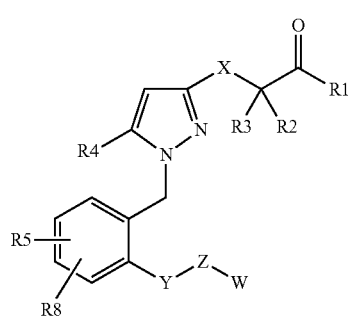

wherein $R_1$ is selected from the group consisting of $OR_7$, $N(R_7)_2$, and $N(R_7)SO_2R_7$ wherein $R_7$ is selected from the group consisting of H, alkyl and aryl, wherein said alkyl and aryl may be substituted with fluoro;

R₂ is selected from the group consisting of H and alkyl;

R₃ is selected from the group consisting of H and alkyl; wherein R₂ and R₃ together can form a cycloalkyl ring;

X is $(CH_2)_n$ wherein n is 0 or an integer of from 1 to 3; provided however that when n is 0 or 1, R₁ is not OR₇ or $N(R_7)_2$;

R₄ is selected from the group consisting of H, alkyl and fluoroalkyl;

R₅ is selected from the group consisting of H, hydroxyl, alkyl, aryl, alkoxy, aryloxy, halogen, nitro, amino, cyano, hydroxyl-substituted alkyl, aryl, alkoxy, or aryloxy, halogen-substituted alkyl, aryl, alkoxy, or aryloxy, nitro-substituted alkyl, aryl, alkoxy, or aryloxy, amino-substituted alkyl, aryl, alkoxy, or aryloxy, or cyano-substituted alkyl, aryl, alkoxy, or aryloxy;

R₆ is selected from the group consisting of H, hydroxyl, alkyl, aryl, alkoxy, aryloxy, halogen, nitro, amino, cyano, hydroxyl-substituted alkyl, aryl, alkoxy, or aryloxy, halogen-substituted alkyl, aryl, alkoxy, or aryloxy, nitro-substituted alkyl, aryl, alkoxy, or aryloxy, amino-substituted alkyl, aryl, alkoxy, or aryloxy, or cyano-substituted alkyl, aryl, alkoxy, or aryloxy;

Z is $(CH_2)_m$ wherein m is 0 or an integer of from 1 to 3;

Y is selected from the group consisting of O, S, SO, SO₂ and $(CH_2)_p$, wherein p is 0 or an integer of from 1 to 3; and W is selected from the group consisting of alkyl and aryl.

2. The compound of claim 1 wherein R₁ is selected from the group consisting of OH and NHSO₂CF₃.

3. The compound of claim 2 wherein R₂ and R₃ are H.

4. The compound of claim 3 wherein R₄ is alkyl.

5. The compound of claim 4 wherein R₄ is methyl.

6. The compound of claim 2 wherein R₆ is H.

7. The compound of claim 6 wherein R₅ is selected from the group consisting of H, alkyl, alkoxy, halogen and fluorinated alkyl and alkoxy.

8. The compound of claim 7 wherein R₅ is selected from the group consisting of chloro, bromo and trifluoromethyl.

9. The compound of claim 2 wherein Z is $(CH_2)_m$ and m is an integer of 1.

10. The compound of claim 2 wherein Y is O.

11. The compound of claim 2 wherein W is alkyl.

12. The compound of claim 11 wherein W is alkyl having from 4 to 7 carbon atoms.

13. A compound selected from the group consisting of N-(3-{1-[5-Chloro-2-(4-chloro-benzyloxy)-benzyl]-5-methyl-1H-pyrazol-3-yl}-propionyl)-C,C,C-trifluoromethanesulfonamide, 3-{1-[5-Chloro-2-(2-ethyl-butoxy)-benzyl]-5-methyl-1H-pyrazol-3-yl}-propionic acid, 3-{1-[5-Bromo-2-(2-ethyl-butoxy)-benzyl]-5-methyl-1H-pyrazol-3-yl}-propionic acid, 3-[1-(5-Bromo-2-cyclopentylmethoxybenzyl)-5-methyl-1H-pyrazol-3-yl]-propionic acid, and, 3-[1-(2-Cyclopentylmethoxy-5-trifluoromethylbenzyl)-5-methyl-1H-pyrazol-3-yl]-propionic acid.

14. A compound selected from the group consisting of

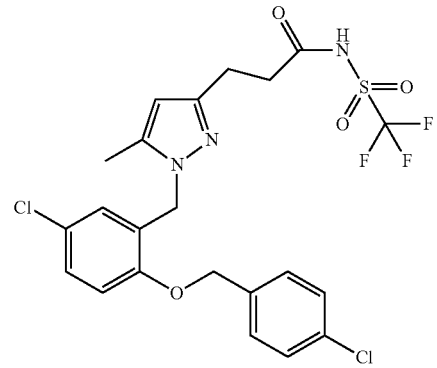

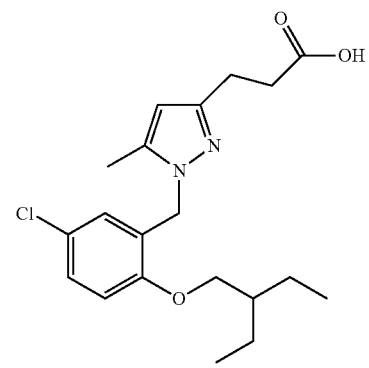 [SMILES: CCC(CC)COc1ccc(Cl)cc1Cn1nc(CCC(=O)O)cc1C]

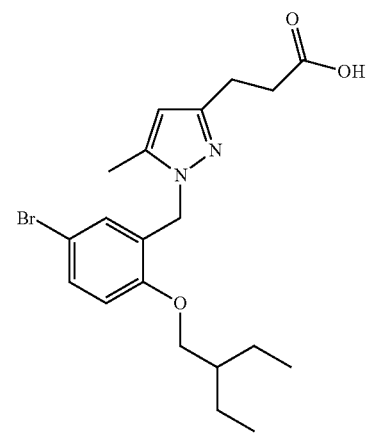

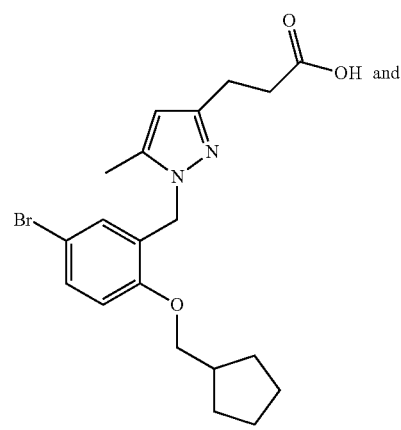

-continued

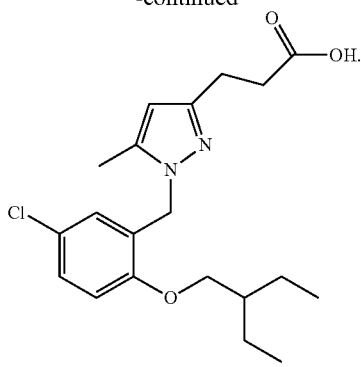

15. A method for decreasing the secretion of a cytokine selected from the group consisting of VEGF, IL-8, MCP-1, TNFα, IL-1α, MDC and RANTES in a patient in need thereof comprising administering to a patient an effective amount of a compound according to formula

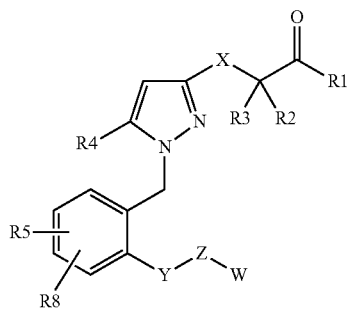

Wherein $R_1$ is selected from the group consisting of $OR_7$, $N(R_7)_2$, and $N(R_7)SO_2R_7$ wherein $R_7$ is selected from the group consisting of H, alkyl and aryl, wherein said alkyl and aryl may be substituted with fluoro;
$R_2$ is selected from the group consisting of H and alkyl;
$R_3$ is selected from the group consisting of H and alkyl; wherein $R_2$ and $R_3$, together, can form a cycloalkyl ring;
X is $(CH_2)_n$ wherein n is 0 or an integer of from 1 to 3, provided however that when n is 0 or 1, $R_1$ is not $OR_7$ or $N(R_7)_2$;
$R_4$ is selected from the group consisting of H, alkyl and fluoroalkyl;
$R_5$ is selected from the group consisting of H, hydroxyl, alkyl, aryl, alkoxy, aryloxy, halogen, nitro, amino, cyano, hydroxyl-substituted alkyl, aryl, alkoxy, or aryloxy, halogen-substituted alkyl, aryl, alkoxy, or aryloxy, nitro-substituted alkyl, aryl, alkoxy, or aryloxy, amino-substituted alkyl, aryl, alkoxy, or aryloxy, or cyano-substituted alkyl, aryl, alkoxy, or aryloxy;
$R_6$ is selected from the group consisting of H, hydroxyl, alkyl, aryl, alkoxy, aryloxy, halogen, nitro, amino, cyano, hydroxyl-substituted alkyl, aryl, alkoxy, or aryloxy, halogen-substituted alkyl, aryl, alkoxy, or aryloxy, nitro-substituted alkyl, aryl, alkoxy, or aryloxy, amino-substituted alkyl, aryl, alkoxy, or aryloxy, or cyano-substituted alkyl, aryl, alkoxy, or aryloxy;
Z is $(CH_2)_m$ wherein m is 0 or an integer of from 1 to 3;
Y is selected from the group consisting of O, S, SO, $SO_2$ and $(CH_2)_p$, wherein p is 0 or an integer of from 1 to 3; and
W is selected from the group consisting of alkyl and aryl.

16. A method according to claim 15 wherein said cytokine is IL-8 and said compound is administered for treating rheumatoid arthritis.

17. A method according to claim 15 wherein said cytokine is MCP-1 and said compound is administered for treating rheumatoid arthritis, psoriasis, atherosclerosis, atopic dermatitis, renal disease, pleurisy, asthma, colitism, endometriosis, polymyositis, dermatomyositis, uveitis, restenosis, and diabetes.

18. A method according to claim 15 wherein said cytokine is MDC and said compound is administered for treating rheumatoid arthritis, inflammation, thrombosis, atherosclerosis, chronic renal failure, chronic liver disease, Alzheimer's disease, and systemic sclerosis.

19. A method according to claim 15 wherein said cytokine is RANTES and said compound is administered for treating rheumatoid arthritis, inflammation, thrombosis, atherosclerosis, asthma, allergic rhinitis, and multiple sclerosis.

20. A method for treating inflammation in a human patient which comprises administering to a patient in need thereof an effective amount of a compound selected from the group consisting of

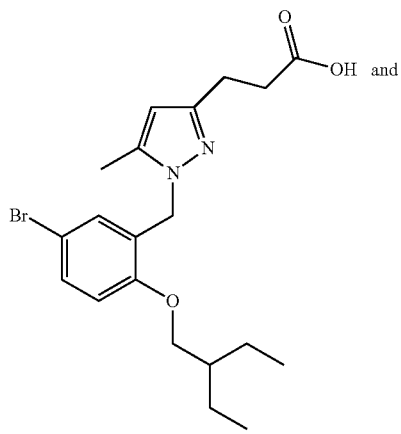

21. A method for treating uveitis in a human patient which comprises administering to a patient in need thereof an effective amount of a compound selected from the group consisting of

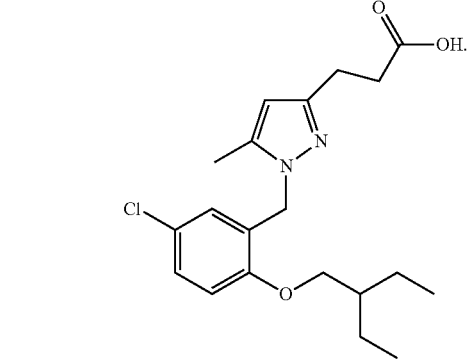

37
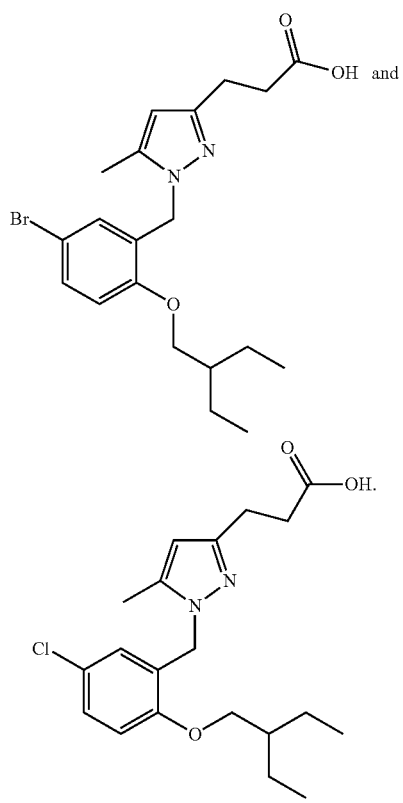
22. A method for treating allergic conjunctivitis in a human patient which comprises administering to a patient in need thereof an effective amount of a compound selected from the group consisting of
38
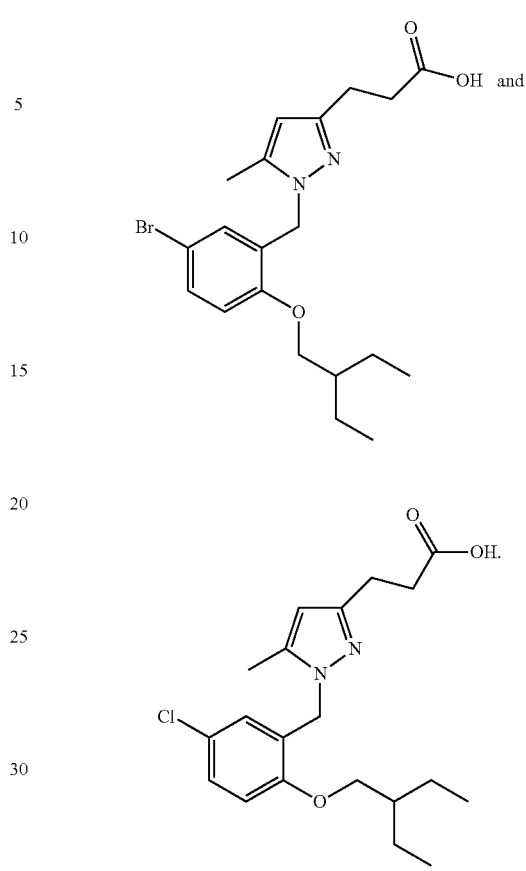
* * * * *